US008114967B2

(12) United States Patent
Bhatt et al.

(10) Patent No.: US 8,114,967 B2
(45) Date of Patent: Feb. 14, 2012

(54) CONSTRUCTS AND LIBRARIES COMPRISING ANTIBODY SURROGATE LIGHT CHAIN SEQUENCES

(75) Inventors: Ramesh Bhatt, Belmont, CA (US); Lawrence Horowitz, Atherton, CA (US); Li Xu, Cupertino, CA (US)

(73) Assignee: Sea Lane Biotechnologies LLC, Atherton, CA (US)

( * ) Notice: Subject to any disclaimer, the term of this patent is extended or adjusted under 35 U.S.C. 154(b) by 561 days.

(21) Appl. No.: 12/056,151

(22) Filed: Mar. 26, 2008

(65) Prior Publication Data
US 2010/0004139 A1  Jan. 7, 2010

Related U.S. Application Data

(60) Provisional application No. 60/920,568, filed on Mar. 27, 2007.

(51) Int. Cl.
C07K 1/00 (2006.01)
C07K 14/00 (2006.01)
C07K 16/00 (2006.01)
C12P 21/08 (2006.01)
G01N 33/00 (2006.01)
C40B 40/02 (2006.01)

(52) U.S. Cl. ......... 530/387.3; 530/350; 530/387.1; 436/512; 436/86

(58) Field of Classification Search .......... 530/350, 530/387.1, 387.3; 436/512, 86
See application file for complete search history.

(56) References Cited

U.S. PATENT DOCUMENTS 5,427,908 A * 6/1995 Dower et al. ............ 506/1
2003/0215453 A1 * 11/2003 Dedera et al. ............ 424/155.1
2006/0147997 A1 * 7/2006 Ramakrishnan ............ 435/7.1

FOREIGN PATENT DOCUMENTS

EP  0 269 127 A  6/1988

OTHER PUBLICATIONS

Hirabayashi et al. (Kinetic analysis of the interactions of recombinant human VpreB and Ig V domains, 1995, The Journal of Immunology, vol. 155, pp. 1218-1228, provided by applicants in IDS).*

Gauthier et al. (u-surrogate light chain physicochemical interactions of the human preB cell receptor: implications for V H repertoire selection and cell signaling at the preB cell stage, 1999, Journal of Immunology, vol. 162, pp. 41-50).*

Kudo et al. (PIR database, 1987, accession No. A26166, accessed on Jul. 19, 2010, SCORE alignment, 4 pages).*

(Continued)

*Primary Examiner* — Christopher M Gross
*Assistant Examiner* — Shannon Janssen
(74) *Attorney, Agent, or Firm* — Arnold & Porter LLP; Ginger R. Dreger

(57) ABSTRACT

The invention concerns constructs and libraries comprising antibody surrogate light chain sequences. In particular, the invention concerns constructs comprising VpreB sequences, optionally partnered with another polypeptide, such as, for example, antibody heavy chain variable domain sequences, and libraries containing the same.

1 Claim, 31 Drawing Sheets
(5 of 31 Drawing Sheet(s) Filed in Color)

Surrogate Light Chain Alignment with Variable and Constant Lambda Light Chains

```
                       1                                                           CDR1         65
NM_007128 VPREB1  (1) MSWAPVLLMLFVYCTGCGPQPVLHQPPAMSSALGTTIRLTCTLRNDHD-IGVYSVYWYQQRPGHP
          VL1_1b  (1) ---------------GSQSVLTQPPSVSAAPGQKVTISCSGSSSNI--GNNYVSWYQQLPGTA
CAA01962 Lambda5  (1) ---------------MKLRVGQTLGTIPRQCEVLLLLLLGLVDGVHHIISPSSAERSRA 66   CDR2                                                   CDR3     130
NM_007128 VPREB1  (65) PRFLLRYFSQSDKSQGPQVPPRFSGSKDVARNRGYLSISELQPEDEAMYCAMGARSSEKEEREP
          VL1_1b  (47) PKLLIYDNNK----RPSGIPDRFSGS--KSGTSATLGITGLQTGDEADYYCGTWDSSLSAVVFGG
CAA01962 Lambda5  (46) VGPGASVGSN-------------RPSLWALPGRLLFQIIPRGAGPRCSFHRLPSKPQFWYVFGG
Vlambda constant   (1) -----------------------------------------------------------G 131                                                                  195
NM_007128 VPREB1 (130) RWEEENEPTAARTRVP------------------------------------------------
CAA01962 Lambda5  (98) GTQLTILGQPKSDPLVTLFLPSLKNLQPTRPHVVCLVSEFYPGTLVVDWKVDGVPVTQGVETTQP
Vlambda constant   (2) GTKLTVLRQPKAAFSVTLFPPSSEELQANKATLVCLISDFYPGAVTVAWKADGSPVKAGVETTTP 196                                         242
Vlambda constant  (67) SKQSNNKYAASSYLSLTPEQWKSHKSYSCQVTHEGSTVEKTVAPTECS
CAA01962 Lambda5 (163) SKQTNNKYMVSSYLTLISDQWMPHSRYSCRVTHEGNTVEKSVSPAECS
```

- VPREB1 shares some sequence similarity to classic lambda light chain variable regions
- Lambda 5 shares similarity to Vlambda constant regions and Framework region 4
- Surrogate light chain has regions that are analogous to CDR regions

OTHER PUBLICATIONS

Minegishi et al. (Novel mechanisms control the folding and assembly of _5/14.1 and VpreB to produce an intact surrogate light chain, 1999, Proc. Natl. Acad. Sci. USA, vol. 96, pp. 3041-3046).*

Hagiwara, S., The Kobe Journal of Medical Sciences, 42(1): 43-59 (1996).

Hirabayashi, Y., et al., Journal of Immunology, 155(3): 1218-1228 (1995).

Lanig, Harald, et al., Molecular Immunology, 40(17): 1263-1272 (2004).

Xu, Li, et al. Proceedings of the National Academy of Sciencees of the Unities States of America, 105(31): 10756-10761 (2008).

Database UniProt (Online), Immunoglobulin Lambda-like Polypeptide 1, XP002498065 (1990).

* cited by examiner

Figure 1

Surrogate Light Chain Alignment with Variable and Constant Lambda Light Chains

```
                                                                                              CDR1                    65
NM_007128 VPREB1  (1) MSWAPVLLMLFVYCTGCGPQPVLHQPPAMSSALGTTIRLTCTLRNDHD-IGVYSVYWYQQRPGHP
           VL1_1b (1) ----------------------GSQSVLTQPPSVSAAPGQKVTISCSGSSSNI--GNNYVSWYQQLPGTA
CAA01962 Lambda5  (1) -------------MKLRVGQTLGTIPRQCEVLLLLLLGLVDGVHHILSPSSAERSRA CDR2                                                      CDR3           130
NM_007128 VPREB1 (65) PRFLLRYFSQSDKSQGPQVPPRFSGSKDVARNRGYLSISELQPEDEAMYYCAMGARSSEKERER
           VL1_1b (47) PKLLIYDNNK----RPSGIPDRFSGS--KSGTSATLGITGLQTGDEADYYCGTWDSSLSAVFGG
CAA01962 Lambda5 (46) VGPGASVGSN-----------RPSLWALPGRLLFQIIPRGAGPRCSPHRLPSKPQFWYVFGG
Vlambda constant  (1) ---------------------------------------------------------------G 195
NM_007128 VPREB1 (130) EWEEEMEPTAARTRVP-----------------------------------------------
CAA01962 Lambda5  (98) GTQLTILGQPKSDPLVTLFLPSLKNLQPTRPHVVCLVSEFYPGTLVVDWKVDGVPVTQGVETTQP
Vlambda constant   (2) GTKLTVLRQPKAAPSVTLFPPSSEELQANKATLVCLISDFYPGAVTVAWKADGSPVKAGVETTTP 242
Vlambda constant  (67) SKQSNNKYAASSYLSLTPEQWKSHKSYSCQVTHEGSTVEKTVAPTECS
CAA01962 Lambda5 (163) SKQTNNKYMVSSYLTLISDQWMPHSRYSCRVTHEGNTVEKSVSPAECS
```

- VPREB1 shares some sequence similarity to classic lambda light chain variable regions
- Lambda 5 shares similarity to Vlambda constant regions and Framework region 4
- Surrogate light chain has regions that are analogous to CDR regions Surrogate Light Chain and Fusion Constructs Surrogate Light Chain Deletion and Single Chain Constructs

Figure 6

SLC Alignment with VL5 Genes

```
                        1                                           45
NM_007128 hu VPREB1  (1)   MSWAPVLLMLFVCTGCGP...
         5b          (1)   ------------------
         5c          (1)   ------------------
         5e          (1)   ------------------

46                                           90
NM_007128 hu VPREB1 (46)   DHD...
         5b         (27)
         5c         (27)
         5e         (27)

91                                          135
NM_007128 hu VPREB1 (91)
         5b        (72)
         5c        (72)
         5e        (72)

136   146
NM_007128 hu VPREB1 (136)  EPTAARTRVP -
         5b        (106)   -----------
         5c        (105)   -----------
         5e        (105)   -----------
```

VPreB1 shares only 56% - 62% (amino acids 2-97) to VL lambda5 germlines

SLC Alignment with Constant Lambda

Lambda5 shares only 62% (amino acids 97-209) to a constant lambda region

Figure 8

SLC Alignment with Constant Kappa

```
                         1                                                    50
CAA01962 Lambda5    (1)  MKLRVGQTLGTIPRQCEVLILILLLGLVDGVHHILSPSSAERSRAVGPGA
Kappa constant      (1)  --------------------------------------------------
                         51                                                  100
CAA01962 Lambda5   (51)  SVGSNRPSIWALPGRLLFQIIPRGAGPRCSPHRLPSKPQFWVFGGGTQL
Kappa constant      (1)  --------------------------------------------------
                         101                                                 150
CAA01962 Lambda5  (101)  TILGQPK DFL TF L LA QPTRPH VC  SEF  GTLV DF     GV
Kappa constant      (1)  ----RTV A SVF   P DE  KSGTAS V   NNE  REAK Q     NA
                         151                                                 200
CAA01962 Lambda5  (151)  PV QG-V  TQPSKQTNNK T    YT  ISDQ MP SR  R   E N---
Kappa constant     (47)  LQ GNSQ  VTEQDSKDST VS ST   SKAD EK KV  E    Q LSS
                         201             215
CAA01962 Lambda5  (198)  TVEK VSP
Kappa constant     (97)  P TK  FNR
```

Lambda5 shares only 35% (amino acids 105-209) to a constant kappa region

Adding Functionality to SLC Components

```
MSWAPVLLML FVYCTGCPQ  PVLHQPPAMS SALGTTIRLT CTLRNDHDIG
MSWAPVLLML FVYCTGCPQ  PVLHQPPAMS SALGTTIRLT CTLRNDHDIG
VYSVYWYQQR PGHPPRFLLR YFSQSDKSQG PQVPPRFSGS KDVARNRGYL
SISELQPEDE AMYYCAMGAR SSEKEERERE WEEEMEPTAA RTRVP
(human VpreB1; CAG30495; 145 amino acids; SEQ ID NO: 1)

MAWTSVLLML LAHLTGCPQ  PMVHQPPSAS SSLGATIRLS CTLSNDHNIG
IYSIYWYQQR PGHPPRFLLR YFSHSDKHQG PDIPPRFSGS KDTARNLGYL
SISELQPEDE AVYYCAVGLR SHEKKRMERE WEGEKSYTDL GS
(mouse VpreB2; P13373; 142 amino acids; SEQ ID NO: 2)

MAWTSVLLML LAHLTGKGTL GVQGFLAPPV ALLCPSDGHA SIFSGCGPQP
MVHQPPSASS SLGATIRLSC TLSNDHNIGI YSIYWYQQRP GHPPRFLLRY
FSHSDKHQGP DIPPRFSGSK DTARNLGYLS ISELQPEDEA VYYCAVGLRS
HEKKRMEREW EGEKSYTDLG S
(mouse VpreB2 splice variant; CAA01964; 171 amino acids; SEQ ID NO: 3)

MACRCLSFLL MGTFLSVSQT VLAQLDALLV FPGQVAQLSC TLSPQHVTIR
DYGVSWYQQR AGSAPRYLLY YRSEEDHHRP ADIPDRFSAA KDEAHNACVL
TISPVQPEDD ADYYCSVGYG FSP
(human VpreB3; CAG30496; 123 amino acids; SEQ ID NO: 4)

MKLRVGQTLG TIPRQCEVLL LLLLLGLVDG VHHILSPSSA ERSRAVGPGA
SVGSNRPSLW ALPGRLLFQI IPRGAGPRCS PHRLPSKPQF WYVFGGGTQL
TILGQPKSDP LVTLFLPSLK NLQPTRPHVV CLVSEFYPGT LVVDWKVDGV
PVTQGVETTQ PSKQTNNKYM VSSYLTLISD QWMPHSRYSC RVTHEGNTVE
KSVSPAECS
(human lambda 5; CAA01962; 209 amino acids; SEQ ID NO: 5)

MRPGTGQGGL EAPGEPGPNL RQRWPLLLLG LAVVTHGLLR PTAASQSRAL
GPGAPGGSSR SSLRSRWGRF LLQRGSWTGP RCWPRGFQSK HNSVTHVFGS
GTQLTVLSQP KATPSVTLFP PSSEELQANK ATLVCLMNDF YPGILTVTWK
ADGTPITQGV EMTTPSKQSN NKYAASSYLS LTPEQWRSRR SYSCQVMHEG
STVEKTVAPA ECS
(human lambda 5-like protein; NP_064455; 213 amino acids; SEQ ID NO: 6)
```

Figure 10 (Part 1)

Lambda5dT
MRPGTGQGGLEAPGEPGPNLRQRWPLLLLGLAVVTHGSVTHVFGSGTQLTVLSQ
PKATPSVTLFPPSSEELQANKATLVCLMNDFYPGILTVTWKADGTPITQGVEMT
TPSKQSNNKYAASSYLSLTPEQWRSRRSYSCQVMHEGSTVEKTVAPAECS
(SEQ ID NO: 7)

VpreB1d
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGA (SEQ ID NO: 8)

B11 HC-HIS+ (neutralizing anti-influenza heavy chain)
METDTLLLWVLLLWVPGSTGDAQMQLQESGPGLVKPSETLSLTCTVSGYSFDSG
YYWGWLRQPPGKGLEWIGSIYHSRNTYYNPSLKSRVTISVDTSKNQFSLQLSSV
TAADTAVYYCARGTWYSSNLRYWFDPWGKGTLVRVSSASTKGPSVFPLAPSSKS
TSGGTAALGCLVKDYFPEPVTVSWNSGALTSGVHTFPAVLQSSGLYSLSSVVTV
PSSSLGTQTYICNVNHKPSNTKVDKRVEPKSCDKTHTCPPCPAPELLGGPSVFL
FPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYT
LPPSREEMTKNQVSLTCLVKGFYPSDIAVEWESNGQPENNYKTTPPVLDSDGSF
FLYSKLTVDKSRWQQGNVFSCSVMHEALHNHYTQKSLSLSPGHHHHHH
(SEQ ID NO: 9)

VpreB1-Lambda5 (Fusion1)
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGARSSVTHVFGSGTQLTVLSQPKATPSVTLFPPSSEELQANKATL
VCLMNDFYPGILTVTWKADGTPITQGVEMTTPSKQSNNKYAASSYLSLTPEQWR
SRRSYSCQVMHEGSTVEKTVAPAECA (SEQ ID NO: 10)

VpreB1-CL (Fusion2)
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKSVARNGYLSISELQPED
EAMYYCAMGARSSVTHVFGSGTQLTVLGQPKAAPSVTLFPPSSXELQANKATLV
CLISDFYPGAVTVAWKADSSPVKAGVETTTPSKQSNNKYAASSYLSLTPEQWKS
HRSYSCQVTHEGSTVEKTVAPAECS (SEQ ID NO: 11)

geneIII VpreB1-Lambda5-E tag Fusion (Fusion 1)
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSVTHVFGSGTQLTVLSQPKATPSVTLFPPSSEELQANKAT
LVCLMNDFYPGILTVTWKADGTPITQGVEMTTPSKQSNNKYAASSYLSLTPEQW
RSRRSYSCQVMHEGSTVEKTVAPAECSGAPVPYPDPLEPR (SEQ ID NO: 12)

Figure 10 (Part 2)

geneIII VpreB1-C1-E tag Fusion (Fusion 2)
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSVTHVFGSGTQLTVLRQPKAAPSVTLFPPSSEELQANKAT
LVCLISDFYPGAVTVAWKADGSPVKAGVETTTPSKQSNNKYAASSYLSLTPEQW
KSHKSYSCQVTHEGSTVEKTVAPTECSGAPVPYPDPLEPR (SEQ ID NO: 13)

pe1B F5 HC gamma-His+ (non-neutralizing anti-influrnza heavy chain)
MKYLLPTAAAGLLLLAAQPAMAQVQLQESGGGLVQPGGSLRLSCAASGFPSSYV
MIWVRQVPGKGLEWVSAIGGSGGSTYYADSVKGRFTISRDNSKNTLYLQMNSLR
ADDTAVYYCVLSPKSYYDNSGIYFDFWGKGTLVRVSSASTKGPSVFPLAPSSLS
TSGGTAALGLVKDYFPEPVTVSWNSGALTSGVHTFPAVLQSSGLYSLSSVVTVP
SSSLGTQTYICNVNHKPSNTKVDKRVEPKSCAAAHHHHHHGEQKLISEEDL
(SEQ ID NO: 14)

pe1B F5 HC mu-His+ (non-neutralizing anti-influrnza IgM heavy chain)
MKYLLPTAAAGLLLLAAQPAMAQVQLQESGGGLVQPGGSLRLSCAASGFPFSSY
VMIWVRQVPGKGLEWVSAIGGSGGSTYYADSVKGRFTISRDNSKNTLYLQMNSL
RADDTAVYYCVLSPKSYYDNSGIYFDFWGKGTLVRVSSGSASAPTLFPLVSCEN
SPSDTSSVAVGCLAQDFLPDSITFSWKYKNNSDISSTRGFPSVLRGGKYAATSQ
VLLPSKDVMQGTDEHVVCKVQHPNGNKEKNVPLPVAAAHHHHHHGEQKLISEED
L (SEQ ID NO: 15)

GAPVPYPDPLEPR (SEQ ID NO: 16)

GEQKLISLEEDL (SEQ ID NO: 17)

geneIII leader VpreB1-E tag full length
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGARSSEKEERREREWEEEMEPTAARTRVPGAPVPYPDPLEPR
(SEQ ID NO: 18)

geneIII leader VpreB1dT
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGA (SEQ ID NO: 19)

geneIII leader VpreB1dT-E tag
VKKLLLFAIPLVVPFYSHSAQPVLHQPPAMSSALGTTIRLTCTLRNDHDIGVYS
VYWYQQRPGHPPRFLLRYFSQSDKSQGPQVPPRFSGSKDVARNRGYLSISELQP
EDEAMYYCAMGAGAPVPYPDPLEPR (SEQ ID NO: 20)

Figure 10 (Part 3)

OmpA leader-Lambda5
MKKTAIAIAVALAGFATVAQAALLRPTAASQSRALGPGAPGGSSRSSLRSRWGR
FLLQRGSWTGPRCWPRGFQSKHNSVTHVFGSGTQLTVLSQPKATPSVTLFPPSS
EELQANKATLVCLMNDFYPGILTVTWKADGTPITQGVEMTTPSKQSNNKYAASS
YLSLTPEQWRSRRSYSCQVMHEGSTVEKTVAPAECS (SEQ ID NO: 21)

OmpA leader-Lambda5dT
MKKTAIAIAVALAGFATVAQAASVTHVFGSGTQLTVLSQPKATPSVTLFPPSSE
ELQANKATLVCLMNDFYPGILTVTWKADGTPITQGVEMTTPSKQSNNKYAASSY
LSLTPEQWRSRRSYSCQVMHEGSTVEKTVAPAECS (SEQ ID NO: 22)

GLP-1 VpreB1 full length
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGARSSEKEEREREWEEEMEPTAARTRVPHAEGTFTSDVSSYLEGQ
AAKEFIAWLVKGR (SEQ ID NO: 23)

GLP-1 VpreB1dT
MSWAPVLLMLFVYCTGCGPQPVLHQPPAMSSALGTTIRLTCTLRNDHDIGVYSV
YWYQQRPGHPPRFLLRYFSQSDKSQGPQVPPRFSGSKDVARNRGYLSISELQPE
DEAMYYCAMGAHAEGTFTSDVSSYLEGQAAKEFIAWLVKGR (SEQ ID NO: 24)

GLP-1 Lambda5 full length
MRPGTGQGGLEAPGEPGPNLRQRWPLLLLHAEGTFTSDVSSYLEGQAAKEFIAW
LVKGRGLAVVTHGLLRPTAASQSRALGPGAPGGSSRSSLRSRWGRFLLQRGSWT
GPRCWPRGFQSKHNSVTHVFGSGTQLTVLSQPKATPSVTLFPPSSEELQANKAT
LVCLMNDFYPGILTVTWKADGTPITQGVEMTTPSKQSNNKYAASSYLSLTPEQW
RSRRSYSCQVMHEGSTVEKTVAPAECS (SEQ ID NO: 25)

GLP-1 Lambda5dT
MRPGTGQGGLEAPGEPGPNLRQRWPLLLLGHAEGTFTSDVSSYLEGQAAKEFIA
WLVKGRLAVVTHGSVTHVFGSGTQLTVLSQPKATPSVTLFPPSSEELQANKATL
VCLMNDFYPGILTVTWKADGTPITQGVEMTTPSKQSNNKYAASSYLSLTPEQWR
SRRSYSCQVMHEGSTVEKTVAPAECS (SEQ ID NO: 26)

Figure 10 (Part 4)

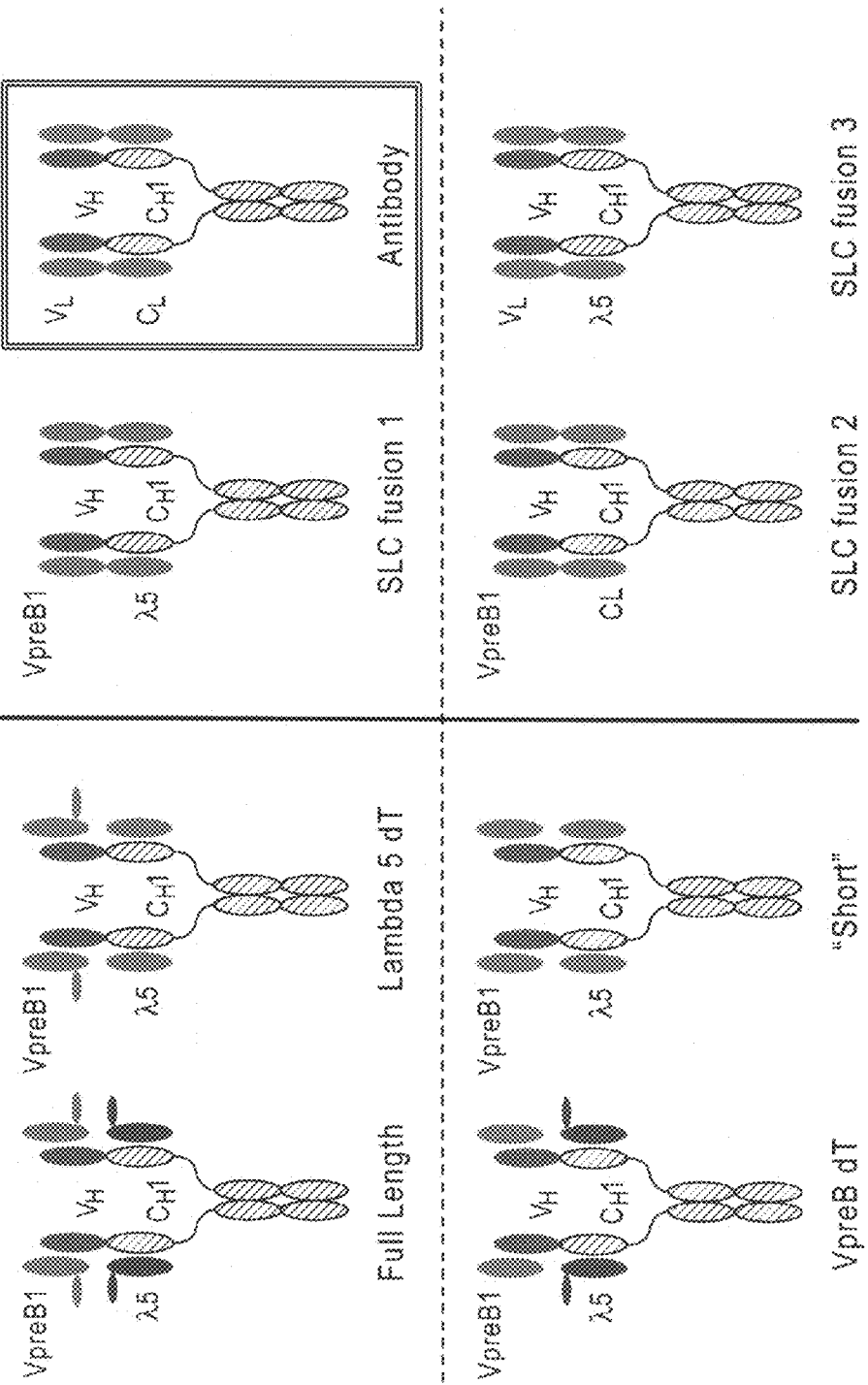

Detection of Surrogate Light Chains and Complexed Heavy Chains

M  Marker
1  Full Length Surrobody
2  Lambda 5 dT Surrobody
3  VpreB dT Surrobody
4  Short Surrobody
5  Surrobody Fusion 1
6  Surrobody Fusion 2
7  Antibody

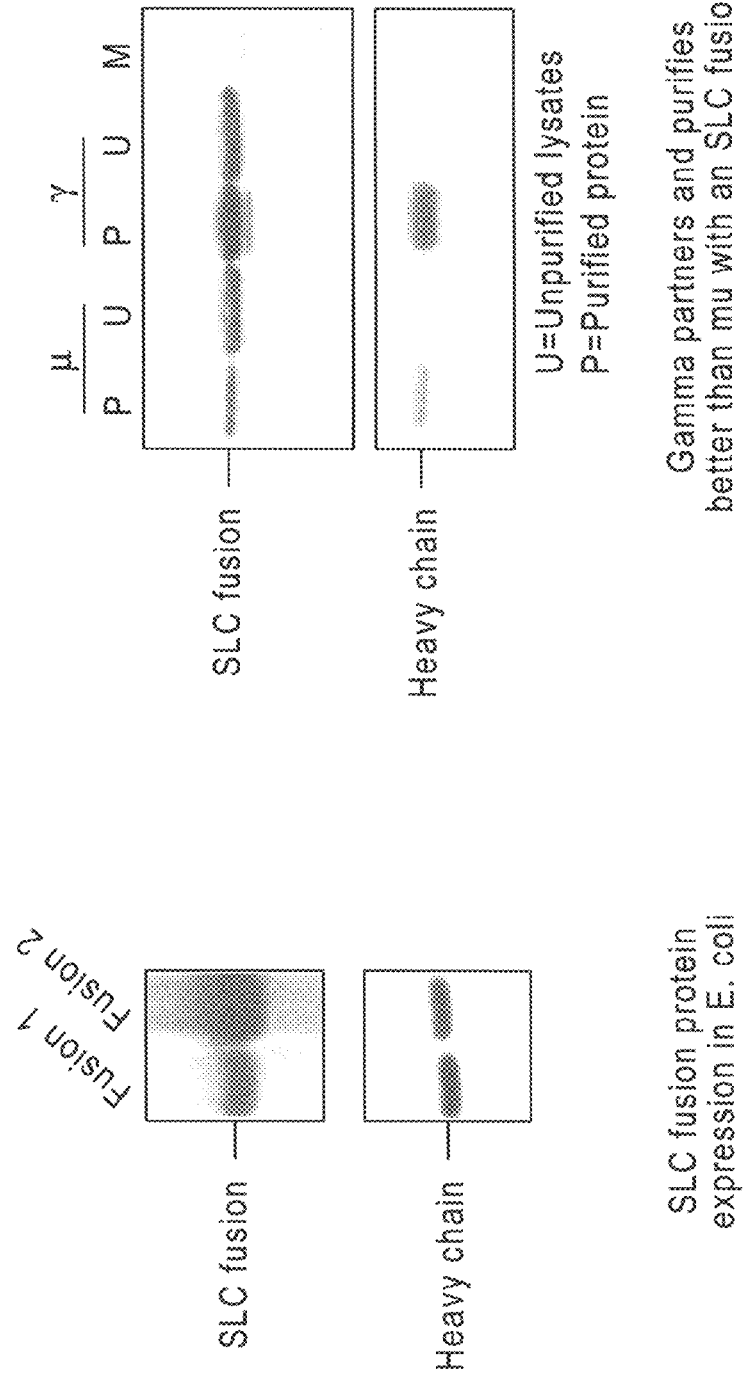

Phage surrobody capture ELISA via anti-phage detection

*Phage expressing either surrogate light chain fusions are immobilized via stable complexes with heavy chain fragments fused to m13 gene III*

Figure 16A

Trimer antigen binding

Supernatants of Mammalian Expressed Surrobody SLC Variants Contain Stable Complexes that Bind Viral Target Heavy chain detection

Figure 16B

VpreB1 detection

Surrobody SLC Fusion Phage Paired with Neutralizing Heavy Chain Readily Binds H5 HA Antig

Figure 19

Surrobody variant pahge paired with neutralizing heavy chain binds antigen

Figure 20

| Number of transformants | Library | Round of panning (fold enrichment) | Percent positive clones |
|---|---|---|---|
| $3.84 \times 10^7$ | Fusion 1 - Influenza | 1 (5x) | 79% |
| | Fusion 1 - Influenza | 2 (97x) | 95% |
| $7.80 \times 10^7$ | Fusion 2 - Influenza | 1 (20x) | 95% |
| | Fusion 2 - Influenza | 2 (48x) | 99% |

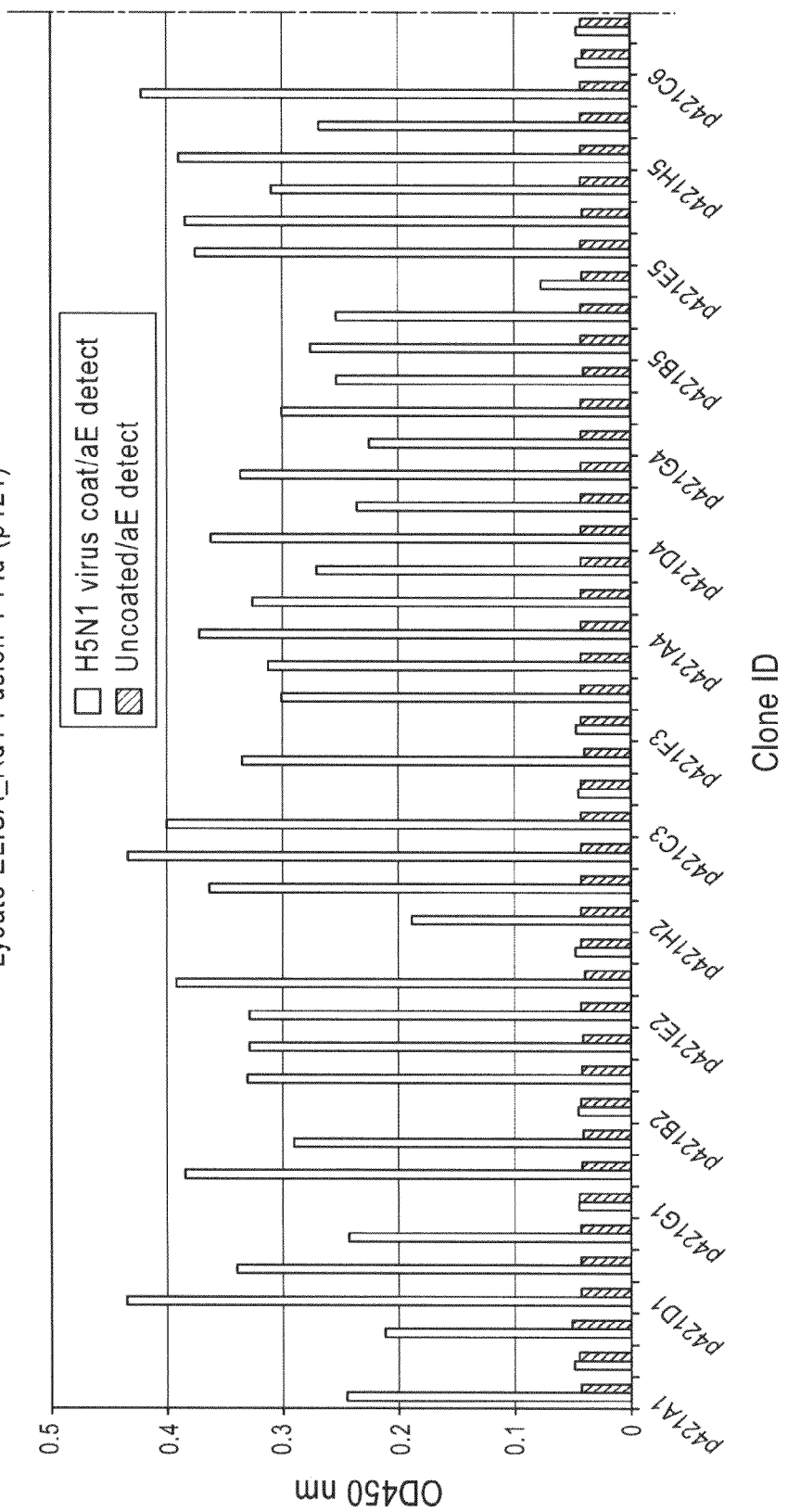

Figure 21A (Part 2)

Clonal analysis of Round 1 Fusion 1 library clones

Lysate ELISA_Rd1 Fusion 1-Flu (p421)

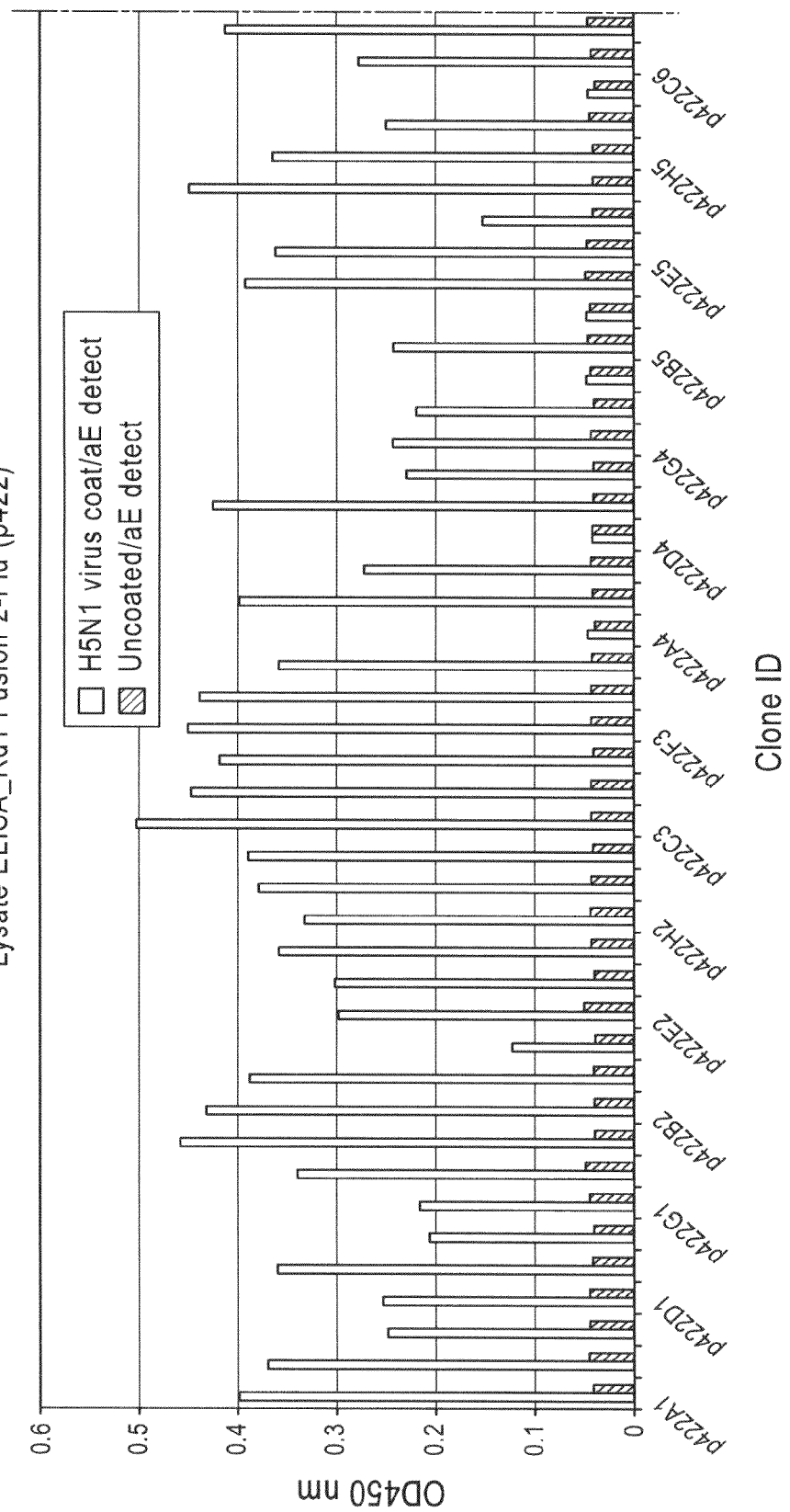

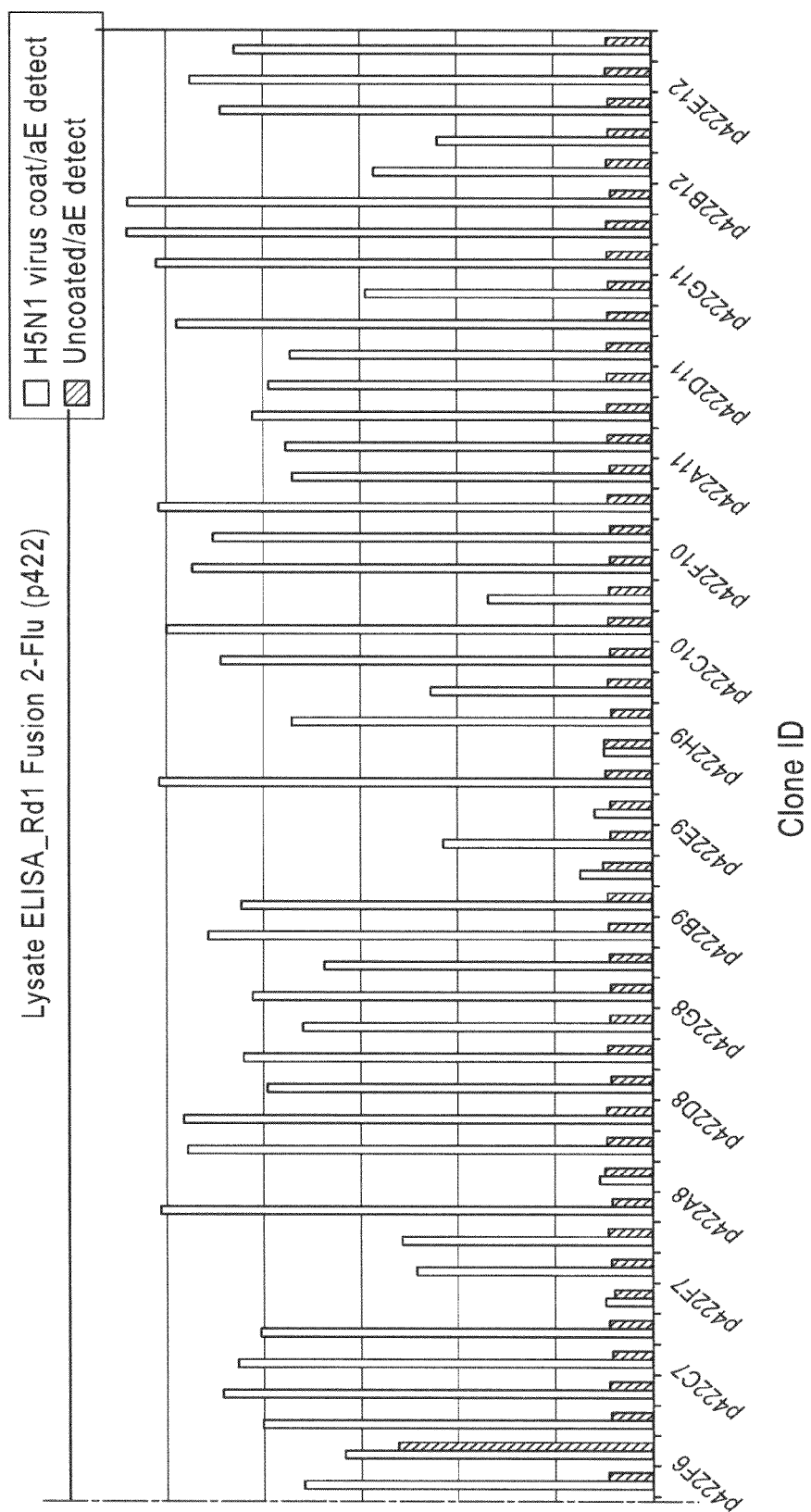
Figure 21B (Part 2)
Clonal analysis of Round 1 Fusion 2 library clones

Figure 22A (Part 1)

Clonal analysis of Round 2 Fusion 1 library clones

Lysate ELISA_Rd1 Fusion 1-Flu (p423)

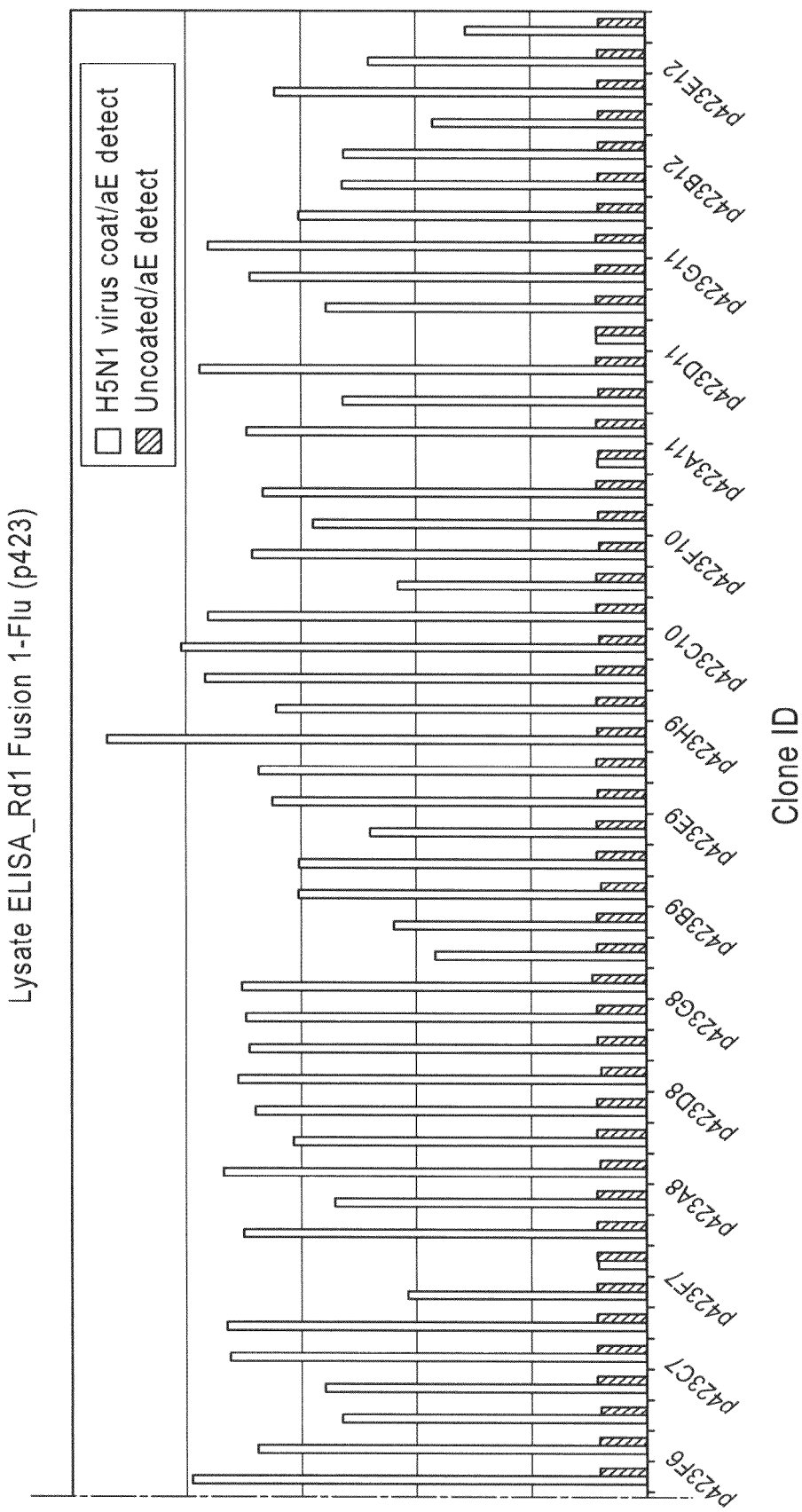
Figure 22A (Part 2)
Clonal analysis of Round 2 Fusion 1 library clones
Lysate ELISA_Rd1 Fusion 1-Flu (p423)

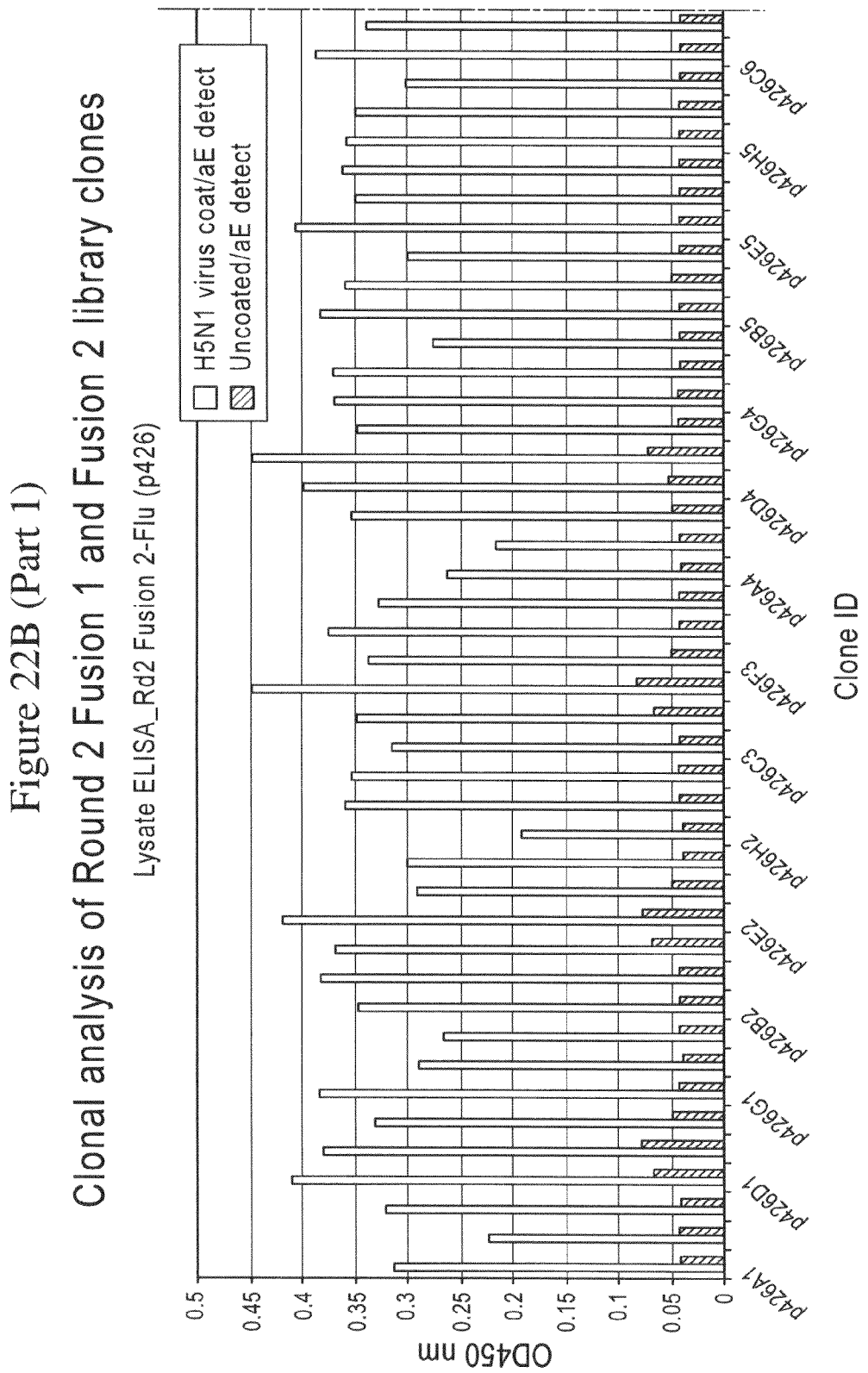
Figure 22B (Part 1)
Clonal analysis of Round 2 Fusion 1 and Fusion 2 library clones
Lysate ELISA_Rd2 Fusion 2-Flu (p426)

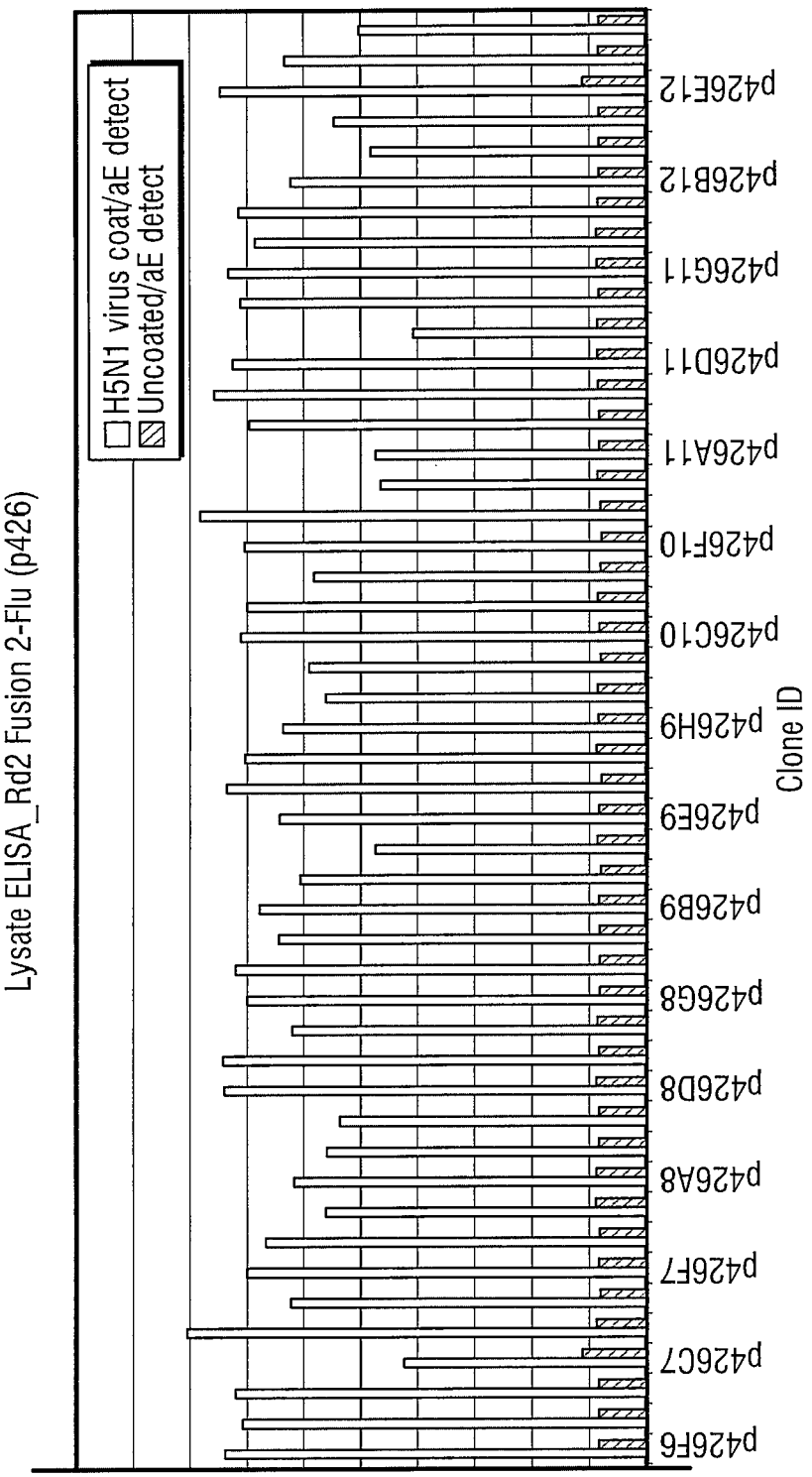

CONSTRUCTS AND LIBRARIES COMPRISING ANTIBODY SURROGATE LIGHT CHAIN SEQUENCES

CROSS-REFERENCE TO RELATED APPLICATIONS

This application claims the benefit of U.S. Provisional Application Ser. No. 60/920,568, filed Mar. 27, 2007, the entire disclosure of which is incorporated herein by reference.

FIELD OF THE INVENTION

The present invention concerns constructs and libraries comprising antibody surrogate light chain sequences. In particular, the invention concerns constructs comprising VpreB sequences, optionally partnered with another polypeptide, such as, for example, antibody heavy chain variable domain sequences, and libraries containing the same.

BACKGROUND OF THE INVENTION

Antibody (Ig) molecules produced by B-lymphocytes are built of heavy (H) and light (L) chains. The amino acid sequences of the amino terminal domains of the H and L chains are variable ($V_H$ and $V_L$), especially at the three hypervariable regions (CDR1, CDR2, CDR3) that form the antigen combining site. The assembly of the H and L chains is stabilized by a disulfide bond between the constant region of the L chain ($C_L$) and the first constant region of the heavy chain ($C_{H1}$) and by non-covalent interactions between the $V_H$ and $V_L$ domains.

In humans and many animals, such as mice, the genes encoding the antibody H and L chains are assembled by stepwise somatic rearrangements of gene fragments encoding parts of the V regions. Various stages of B lymphocyte development are characterized by the rearrangement status of the Ig gene loci (see, e.g. Melchers, F. & Rolink, A., *B-Lymphocyte Development and Biology*, Paul, W. E., ed., 1999, Lippincott, Philadelphia).

Precursors of B cells (pre-B cells) have been identified in the bone marrow as lymphocytes that produce μ heavy chains but instead of the fully developed light chains express a set of B lineage-specific genes called VpreB(1-3) and λ5, respectively.

The main isoform of human VpreB1 (CAG30495) is a 145 aa-long polypeptide (SEQ ID NO: 1). It has an Ig V domain-like structure, but lacks the last β-strand (β7) of a typical V domain, and has a carboxyl terminal end that shows no sequence homologies to any other proteins. VpreB2 has several isoforms, including a 142-amino acid mouse VpreB2 polypeptide (P13373; SEQ ID NO: 2), and a 171-amino acid long splice variant of the mouse VpreB2 sequence (CAA019641 SEQ ID NO: 3). VpreB1 and VpreB2 sequences have been disclosed in EP 0 269 127 and U.S. Pat. No. 5,182,205; Collins et al., *Genome Biol.* 5(10):R84 (2004); and Hollins et al., *Proc. Natl. Acad. Sci. USA* 86(14): 5552-5556 (1989). The main isoform of human VpreB3 (SEQ ID NO: 4) is a 123 amino acid long protein (CAG30496), disclosed in Collins et al., *Genome Biol.* 5(10):R84 (2004).

VpreB(1-3) are non-covalently associated with another protein, λ5. The human λ5 is a 209-amino acid polypeptide (CAA01962; SEQ ID NO: 5), that carries an Ig C domain-like structure with strong homologies to antibody light chains and, towards its amino terminal end, two functionally distinct regions, one of which shows strong homology to the β7 strand of the Vλ domains. A human λ5-like protein has 213 amino acids (NP_064455; SEQ ID NO: 6) and shows about 84% sequence identity to the antibody λ light chain constant region.

For further details, see the following review papers: Karasuyama et al., *Adv. Immunol.* 63:1-41 (1996); Melchers et al., *Immunology Today* 14:60-68 (1993); and Melchers, *Proc. Natl. Acad. Sci. USA* 96:2571-2573 (1999).

The VpreB and λ5 polypeptides together form a non-covalently associated, Ig light chain-like structure, which is called the surrogate light chain or pseudo light chain. On the surface of early preB cells, the surrogate light chain is disulfide-linked to membrane-bound Ig μ heavy chain in association with a signal transducer CD79a/CD79b heterodimer to form a B cell receptor-like structure, the so-called preB cell receptor (preBCR).

SUMMARY OF THE INVENTION

In one aspect, the invention concerns polypeptides comprising a VpreB sequence or a λ5 sequence conjugated to a heterogeneous amino acid sequence, wherein the polypeptides are capable of binding to a target.

In a preferred embodiment, the polypeptide comprises a VpreB sequence, where VpreB may be any native VpreB, including human VpreB1 (SEQ ID NO: 1), mouse VpreB2 (SEQ ID NO: 2 and 3) and human VpreB3. (SEQ ID NO: 4), or a homologue thereof in another mammalian species, or a fragment or variant thereof, provided that the polypeptide retains the ability to bind to a target.

In a preferred embodiment, the heterogeneous amino acid sequence is a λ5 sequence, which may be any native λ5 sequence, or any fragment or variant thereof, including the native human λ5 sequence of SEQ ID NO: 5, the human λ5-like sequence of SEQ ID NO: 6, and fragments and variants thereof.

The VpreB sequence and the heterogeneous amino acid sequence, e.g. the λ5 sequence, may be directly fused to each other, or may be non-covalently associated. In the former case, the fusion preferably takes place at or around the CDR3 analogous regions of VpreB and λ5, respectively.

In another embodiment, the heterogeneous amino acid sequence is or comprises an antibody light chain variable region sequence. In a particular embodiment, the antibody light chain variable region sequence is fused to the VpreB sequence at a site analogous to an antibody light chain CDR3 region. In another embodiment, the fusion is between the CDR3 region of an antibody light chain and the CDR3 analogous region of a VpreB. In all embodiments, the antibody light chain can be a λ chain or a κ chain.

In particular embodiments, the polypeptides herein, including, without limitation, VpreB-λ5 conjugates (including fusions, other covalent linkage, and non-covalent associations), and VpreB-antibody light chain conjugates, may be further associated with a sequence comprising an antibody heavy chain variable region sequence, such as an antibody heavy chain variable region, or a complete antibody heavy chain, including a variable region.

When the polypeptide comprises a λ5 sequence, λ5 may be any native λ5, including human λ5 of SEQ ID NO: 5 and human λ5-like protein of SEQ ID NO: 6, or a homologue in another mammalian species, or any fragment or variant thereof, provided that the polypeptide retains the ability to bind to a target. In a particular embodiment, the heterogeneous amino acid sequence conjugated to the λ5 sequence is a VpreB sequence.

In the polypeptide constructs of the present invention, the VpreB and λ5 sequences, if both present, may be conjugates by any means, including direct fusion, covalent linkage by a linker sequence (e.g. a peptide linker), and non-covalent association.

In a particular embodiment, a fusion of a VpreB sequence and a λ5 sequence is conjugated to an antibody heavy chain sequence by non-covalent association, to form a dimeric complex.

In another embodiment, a trimeric complex is formed by non-covalent association of a VpreB sequence, a λ5 sequence and an antibody heavy chain sequence. In certain embodiments, in these structures, which are also referred to as variant surrogate light chain structures of "SURROBODY™ variants," the characteristic tails (appendages) of one or both of the VpreB and λ5 portions may be (but do not have to be) retained. It is possible to attach additional functionalities to such appendages. In addition, in various embodiments, beneficial appendage fusions can be designed and made in order to improve various properties of the constructs, such as PK and/or potency.

In all embodiments, when an antibody heavy chain comprising variable region sequences is present, the polypeptide of the present invention and the antibody heavy chain variable region sequences may bind to the same or to different targets.

In another aspect, the invention concerns a library of such polypeptides.

In yet another aspect, the invention concerns a library of such polypeptides associated with antibody heavy chains or fragments thereof comprising variable region sequences.

In a further aspect, the invention concerns a library comprising a collection of surrogate light chain sequences optionally associated with antibody heavy chain variable region sequences.

In all aspects, the library may be in the form of a display, such as, for example, a phage display, bacterial display, yeast display, ribosome display, mRNA display, DNA display, display on mammalian cells, spore display, viral display, display based on protein-DNA linkage, or microbead display.

The invention further concerns various uses of such polypeptides and libraries containing such polypeptides, for example, to design or select antibody-like molecules with desired binding specificities and/or binding affinities, which have important therapeutic applications.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

FIG. 1 shows the alignment of human VpreB1 (SEQ ID NO: 1) and human λ5 (SEQ ID NO: 5) with antibody λ chain variable (SEQ ID NO: 27) and constant regions (SEQ ID NO: 28). VpreB1 shares some sequence similarity to antibody λ chain variable regions, while λ5 shares some similarly to antibody λ chain constant regions and framework region 4. The boxed regions identify VpreB1 and λ5 sequences that are similar to antibody λ chain CDR1, CDR2 and CDR3 regions, respectively.

FIG. 6 is the alignment of human VpreB1 (SEQ ID NO: 1) sequence with antibody λ5 light chain variable region germline sequences (SEQ ID NOs: 29, 30 and 31, respectively). Regions with the highest degree of sequence similarity are boxed. As shown in the figure, VpreB1 shows only 56%-62% (amino acids 2 to 97) sequence identity to the λ5 light chain variable region germline sequences.

FIG. 8 is the alignment of λ5 sequence (SEQ ID NO: 5) with an antibody κ light chain constant region sequence (SEQ ID NO: 33). As shown in the figure, the aligned λ5 sequence shows only 35% (amino acids 105 to 209) sequence identity to the corresponding antibody κ light chain constant region sequence.

FIG. 10 (Parts 1-4) show the human VpreB1 sequence of SEQ ID NO: 1. the mouse VpreB2 sequences of SEQ ID NOS: 2 and 3; the human VpreB3 sequence of SEQ ID NO: 4, the human λ5 sequence of SEQ D NO: 5 and the human λ5-like protein sequence of SEQ ID NO: 6, and sequences of various constructs used in the examples (SEQ ID NOs: 7-26).

FIG. 11 illustrates various trimeric and dimeric surrogate light chain constructs of the invention.

FIGS. 13A and B: SLC fusion proteins express and secrete well into the periplasm of *E. coli* and are best partnered with heavy chain CH1 from IgG1 rather than IgM. FIG. 13A: SCL fusion protein expression in *E. coli*. FIG. 13B: IgG1 gamma chain partners and purifies better than IgM μ chain with an SLC fusion.

FIGS. 16A and B: Purified surrogate light chain constructs expressed in mammalian cells contain stable complexes that bind viral antigen.

FIG. 19: Surrogate light chain construct phage paired with neutralizing heavy chain binds antigen.

FIG. 20: Table summarizing the results of phage display experiments.

FIGS. 21A and B (Parts 1 and 2) show results of clonal analysis of Round 1, Fusions 1 and 2 library clones. FIGS. 22A and B (Parts 1 and 2) show results of clonal analysis of Round 2, Fusions 1 and 2 library clones.

DETAILED DESCRIPTION OF THE INVENTION

A. Definitions

Figure 2:
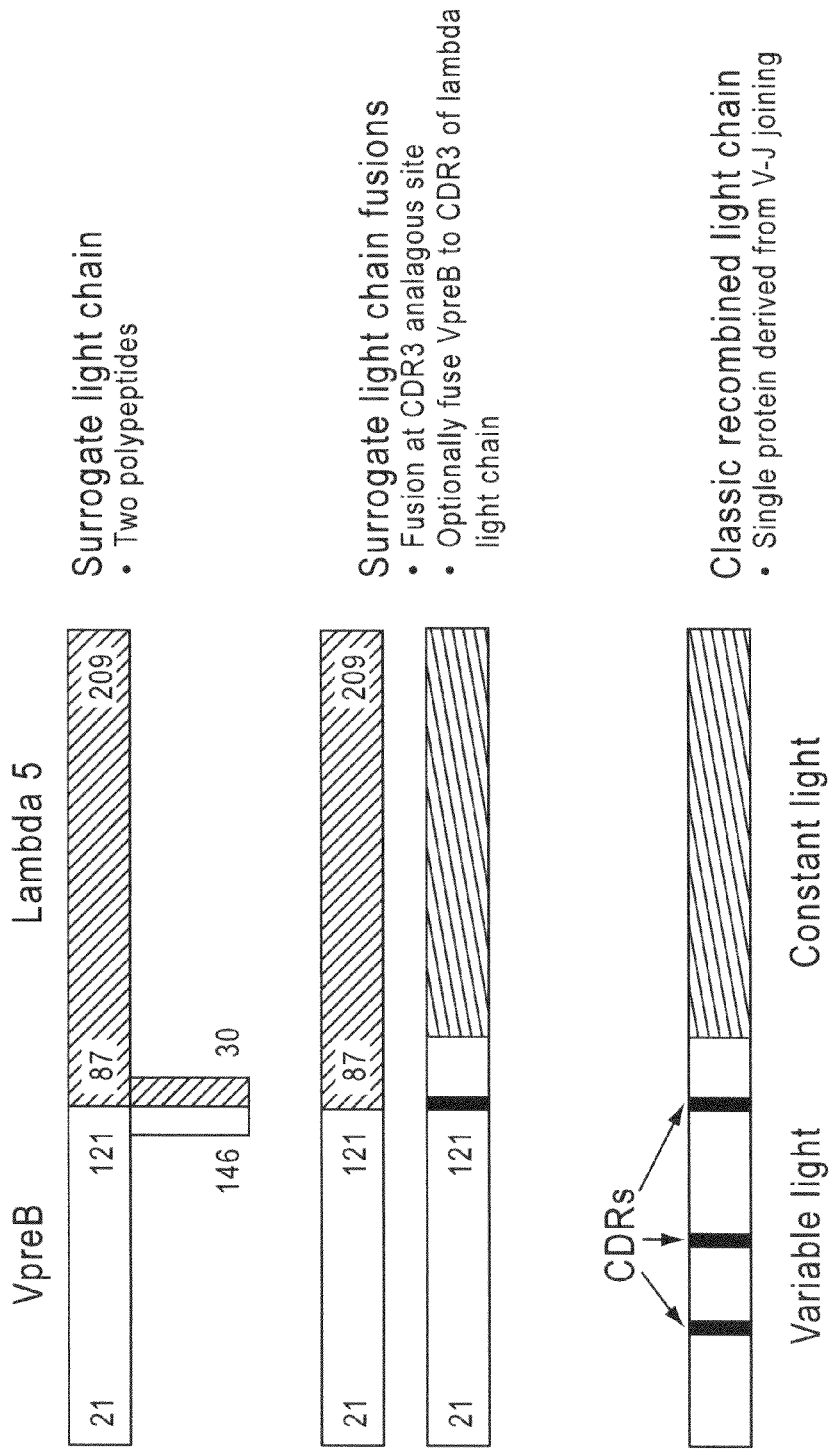
FIG. 2 is a schematic illustration of a surrogate light chain formed by VpreB and λ5 sequences, illustrative fusion polypeptides comprising surrogate light chain sequences, and an antibody light chain structure derived from V-J joining.

Unless defined otherwise, technical and scientific terms used herein have the same meaning as commonly understood by one of ordinary skill in the art to which this invention belongs. Singleton et al., *Dictionary of Microbiology and Molecular Biology* 2nd ed., J. Wiley & Sons (New York, N.Y. 1994), provides one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

The term "surrogate light chain," as used herein, refers to a dimer formed by the non-covalent association of a VpreB and a λ5 protein.

The term "VpreB" is used herein in the broadest sense and refers to any native sequence or variant VpreB polypeptide, specifically including, without limitation, human VpreB1 of SEQ ID NO: 1, mouse VpreB2 of SEQ ID NOS: 2 and 3, human VpreB3 of SEQ ID NO: 4 and isoforms, including splice variants and variants formed by posttranslational modifications, other mammalian homologues thereof, as well as variants of such native sequence polypeptides.

The term "λ5" is used herein in the broadest sense and refers to any native sequence or variant λ5 polypeptide, specifically including, without limitation, human λ5 of SEQ ID NO: 5, human λ5-like protein of SEQ ID NO: 6, and their isoforms, including splice variants and variants formed by posttranslational modifications, other mammalian homologous thereof, as well a variants of such native sequence polypeptides.

The terms "variant VpreB polypeptide" and "a variant of a VpreB polypeptide" are used interchangeably, and are defined herein as a polypeptide differing from a native sequence VpreB polypeptide at one or more amino acid positions as a result of an amino acid modification. The "variant VpreB polypeptide," as defined herein, will be different from a native antibody λ or κ light chain sequence, or a fragment thereof. The "variant VpreB polypeptide" will preferably retain at least about 65%, or at least about 70%, or at least about 75%, or at least about 80%, or at least about 85%, or at least about 90%, or at least about 95%, or at least about 98% sequence identity with a native sequence VpreB polypeptide. In another preferred embodiment, the "variant VpreB polypeptide" will be less then 95%, or less than 90%, or less then 85%, ore less than 80%, or less than 75%, or less then 70%, or less than 65%, or less than 60% identical in its amino acid sequence to a native antibody λ or κ light chain sequence. Variant VpreB polypeptides specifically include, without limitations VpreB polypeptides in which the non-Ig-like unique tail at the C-terminus of the VpreB sequence is partially or completely removed.

The terms "variant λ5 polypeptide" and "a variant of a λ5 polypeptide" are used interchangeably, and are defined herein as a polypeptide differing from a native sequence λ5 polypeptide at one or more amino acid positions as a result of an amino acid modification. The "variant λ5 polypeptide," as defined herein, will be different from a native antibody λ or κ light chain sequence, or a fragment thereof. The "variant λ5 polypeptide" will preferably retain at least about 65%, or at least about 70%, or at least about 75%, or at least about 80%, or at least about 85%, or at least about 90%, or at least about 95%, or at least about 98% sequence identity with a native sequence λ5 polypeptide. In another preferred embodiment, the "variant λ5 polypeptide" will be less then 95%, or less than 90%, or less than 85%, ore less than 80%, or less than 75%, or less then 70%, or less than 65%, or less than 60% identical in its amino acid sequence to a native antibody λ or κ light chain sequence. Variant λ5 polypeptides specifically include, without limitation, λ5 polypeptides in which the unique tail at the N-terminus of the λ5 sequence is partially or completely removed.

Percent amino acid sequence identity may be determined using the sequence comparison program NCBI-BLAST2 (Altschul et al., Nucleic Acids Res. 25:3389-3402 (1997)).

The NCBI-BLAST2 sequence comparison program may be downloaded or otherwise obtained from the National Institute of Health, Bethesda, MD. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

The term "VpreB sequence" is used herein to refer to the sequence of "VpreB," as hereinabove defined, or a fragment thereof.

The term "λ5 sequence" is used herein to refers to the sequence of "λ5," as hereinabove defined, or a fragment thereof.

The term "surrogate light chain sequence," as defined herein, means any polypeptide sequence that comprises a "VpreB sequence" and/or a "λ5 sequence," as hereinabove defined. The "surrogate light chain sequence," as defined herein, specifically includes, without limitation, the human VpreB1 sequence of SEQ ID NO 1, the mouse VpreB2 sequences of SEQ ID NOS: 2 and 3, and the human VpreB3 sequence of SEQ ID NO: 4. and their various isoforms, including splice variants and variants formed by posttranslational modifications, homologues thereof in other mammalian species, as well as fragments and variants thereof. The term "surrogate light chain sequence" additionally includes, without limitation, the human λ5 sequence of SEQ ID NO: 5. the human λ5-like sequence of SEQ ID NO: 6, and their isoforms, including splice variants and variants formed by posttranslational modifications, homologues thereof in other mammalian species, as well as fragments and variants thereof. The term "surrogate light chain sequence" additionally includes a sequence comprising both VpreB and λ5 sequences as hereinabove defined.

For the three-dimensional structure of the pre-B-cell receptor (pre-BCR), including the structure of the surrogate light chain (SCL) and its components see, e.g. Lanig et al., *Mol. Immunol.* 40(17):1263-72 (2004).

The "surrogate light chain sequence" may be optionally conjugated to a heterogeneous amino acid sequence, or any other heterogeneous component, to form a "surrogate light chain construct" herein. Thus, the term, "surrogate light chain construct" is used in the broadest sense and includes any and all additional heterogeneous components, including a heterogeneous amino acid sequence, nucleic acid, and other molecules conjugated to a surrogate light chain sequence, wherein "conjugation" is defined below. A "surrogate light chain construct" is also referred herein as a "SURROBODY™," and the two terms are used interchangeably.

In the context of the polypeptides of the present invention, the term "heterogeneous amino acid sequence," relative to a first amino acid sequence, is used to refer to an amino acid sequence not naturally associated with the first amino acid sequence, at least not in the form it is present in the surrogate light chain constructs herein. Thus, a "heterogenous amino acid sequence" relative to a VpreB is any amino acid sequence not associated with native VpreB in its native environment, including, without limitation, λ5 sequences that are different from those λ5 sequences that, together with VpreB, form the surrogate light chain on developing B cells, such as amino acid sequence variants, e.g. truncated and/or derivatized λ5 sequences. A "heterogeneous amino acid sequence" relative to a VpreB also includes λ5 sequences covalently associated with, e.g. fused to, VpreB, including native sequence λ5, since in their native environment, the VpreB and λ5 sequences are not covalently associated, e.g. fused, to each other. Heterogeneous amino acid sequences also include, without limitation, antibody sequences, including antibody and heavy chain sequences and fragments thereof, such as, for example, antibody light and heavy chain variable region sequences, and antibody light and heavy chain constant region sequences.

The terms "conjugate," "conjugated," and "conjugation" refer to any and all forms of covalent or non-covalent linkage, and include, without limitation, direct genetic or chemical fusion, coupling through a linker or a cross-linking agent, and non-covalent association, for example through Van der Waals forces, or by using a leucine zipper.

The term "fusion" is used herein to refer to the combination of amino acid sequences of different origin in one polypeptide chain by in-frame combination of their coding nucleotide sequences. The term "fusion" explicitly encompasses internal fusions, i.e., insertion of sequences of different origin within a polypeptide chain, in addition to fusion to one of its termini.

As used herein, the term "target" is a substance that interacts with a polypeptide herein. Targets, as defined herein, specifically include antigens with which the VpreB-containing constructs of the present invention interact. Preferably, interaction takes place by direct binding.

As used herein, the terms "peptide," "polypeptide" and "protein" all refer to a primary sequence of amino acids that are joined by covalent "peptide linkages." In general, a peptide consists of a few amino acids, typically from about 2 to about 50 amino acids, and is shorter than a protein. The term "polypeptide," as defined herein, encompasses peptides and proteins.

The term "amino acid" or "amino acid residue" typically refers to an amino acid having its art recognized definition such as an amino acid selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val) although modified, synthetic, or rare amino acids may be used as desired. Thus, modified and unusual amino acids listed in 37 CFR 1.822(b)(4) are specifically included within this definition and expressly incorporated herein by reference. Amino acids can be subdivided into various sub-groups. Thus, amino acids can be grouped as having a nonpolar side chain (e.g., Ala, Cys, Ile, Leu, Met, Phe, Pro, Val); a negatively charged side chain (e.g., Asp, Glu); a positively charged side chain (e.g., Arg, His, Lys); or an uncharged polar side chain (e.g., Asn, Cys, Gln, Gly, His, Met, Phe, Ser, Thr, Trp, and Tyr). Amino acids can also be grouped as small amino acids (Gly, Ala), nucleophilic amino acids (Ser, His, Thr, Cys), hydrophobic amino acids (Val, Leu, Ile, Met, Pro), aromatic amino acids (Phe, Tyr, Trp, Asp, Glu), amides (Asp, Glu), and basic amino acids (Lys, Arg).

The term "polynucleotide(s)" refers to nucleic acids such as DNA molecules and RNA molecules and analogs thereof (e.g., DNA or RNA generated using nucleotide analogs or using nucleic acid chemistry). As desired, the polynucleotides may be made synthetically, e.g., using art-recognized nucleic acid chemistry or enzymatically using, e.g., a polymerase, and, if desired, be modified. Typical modifications include methylation, biotinylation, and other art-known modifications. In addition, the nucleic acid molecule can be single-stranded or double-stranded and, where desired, linked to a detectable moiety.

The term "variant" with respect to a reference polypeptide refers to a polypeptide that possesses at least one amino acid mutation or modification (i.e., alteration) as compared to a native polypeptide. Variants generated by "amino acid modifications" can be produced, for example, by substituting, deleting, inserting and/or chemically modifying at least one amino acid in the native amino acid sequence.

An "amino acid modification" refers to a change in the amino acid sequence of a predetermined amino acid sequence. Exemplary modifications include an amino acid substitution, insertion and/or deletion.

An "amino acid modification at" a specified position, refers to the substitution or deletion of the specified residue, or the insertion of at least one amino acid residue adjacent the specified residue. By insertion "adjacent" a specified residue is meant insertion within one to two residues thereof. The insertion may be N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). Substitution with one or more non-naturally occurring amino acid residues is also encompassed by the definition of an amino acid substitution herein.

A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. *Meth. Enzym.* 202:301 336 (1991). To generate such non-naturally occurring amino acid residues, the procedures of Noren et al. *Science* 244:182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as disclosed above.

An "amino acid deletion" refers to the removal of at least one amino acid residue from a predetermined amino acid sequence.

The term "mutagenesis" refers to, unless otherwise specified, any art recognized technique for altering a polynucleotide or polypeptide sequence. Preferred types of mutagenesis include error prone PCR mutagenesis, saturation mutagenesis, or other site directed mutagenesis.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the single-stranded phage DNA, and the resulting double-stranded DNA is transformed into a phage-supporting host bacterium. Cultures of the transformed bacteria are plated in top agar, permitting plaque formation from single cells that harbor the phage. Theoretically, 50% of the new plaques will contain the phage having, as a single strand, the mutated form; 50% will have the original sequence. Plaques of interest are selected by hybridizing with kinased synthetic primer at a temperature that permits hybridization of an exact match, but at which the mismatches with the original strand are sufficient to prevent hybridization. Plaques that hybridize with the probe are then selected, sequenced and cultured, and the DNA is recovered.

In the context of the present invention, the term "antibody" (Ab) is used to refer to a native antibody from a classically recombined heavy chain derived from V(D)J gene recombination and a classically recombined light chain also derived from VJ gene recombination, or a fragment thereof.

A "native antibody" is heterotetrameric glycoprotein of about 150,000 daltons, composed of two identical light (L) chains and two identical heavy (H) chains. Each light chain is linked to a heavy chain by covalent disulfide bond(s), while the number of disulfide linkages varies between the heavy chains of different immunoglobulin isotypes. Each heavy and light chain also has regularly spaced intrachain disulfide bridges. Each heavy chain has, at one end, a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains, Chothia et al., *J. Mol. Biol.* 186:651 (1985); Novotny and Haber, *Proc. Natl. Acard. Sci. U.S.A.* 82:4592 (1985).

The tern "variable" with reference to antibody chains is used to refer to portions of the antibody chains which differ extensively in sequence among antibodies and participate in the binding and specificity of each particular antibody for its particular antigen. Such variability is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health. Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen-binding. The hypervariable region comprises amino acid residues from a "complementarity determining region" or "CDR" (i.e., residues 30-36 (L1), 46-55 (L2) and 86-96 (L3) in the light chain variable domain and 30-35 (H1), 47-58 (H2) and 93-101 (H3) in the heavy chain variable domain; MacCallum et al., *J. Mol Biol.* 262(5):732-45 (1996).

The term "framework region" refers to the art recognized portions of an antibody variable region that exist between the more divergent CDR regions. Such framework regions are typically referred to as frameworks 1 through 4 (FR1, FR2, FR3, and FR4) and provide a scaffold for holding, in three-dimensional space, the three CDRs found in a heavy or light chain antibody variable region, such that the CDRs can form an antigen-binding surface.

Depending on the amino acid sequence of the constant domain of their heavy chains, antibodies can be assigned to different classes. There are five major classes of antibodies IgA, IgD, IgE, IgG, and IgM, and several of these may be further divided into subclasses (isotypes), e.g., IgG1, IgG2, IgG3, IgG4, IgA, and IgA2.

The heavy-chain constant domains that correspond to the different classes of immunoglobulins are called α, δ, ε, γ, and μ, respectively.

The "light chains" of antibodies from any vertebrate species can be assigned to one of two clearly distinct types, called kappa (κ) and lambda (λ), based on the amino acid sequences of their constant domains. Any reference to an antibody light chain herein includes both κ and λ light chains.

"Antibody fragments" comprise a portion of a full length antibody, generally the antigen binding or a variable domain thereof. Examples of antibody fragments include, but are not limited to, Fab, Fab', F(ab')$_2$, scrv, and (scFv)$_2$ fragments.

As used herein the term "antibody binding region" refers to one or more portions of an immunoglobulin or antibody variable region capable of binding an antigen(s). Typically, the antibody binding region is, for example, an antibody light chain (VL) (or variable region thereof), an antibody heavy chain (VH) (or variable region thereof), a heavy chain Fd region, a combined antibody light and heavy chain (or variable region thereof such as a Fab, F(ab')$_2$, single domain, or single chain antibody (scFv), or a full length antibody, for example, an IgG (e.g., an IgG1, IgG2, IgG3, or IgG4 subtype), IgA1, IgA2, IgD, IgE, or IgM antibody.

The term "epitope" as used herein, refers to a sequence of at least about 3 to 5, preferably at least about 5 to 10, or at least about 5 to 15 amino acids, and typically not more than about 500, or about 1,000 amino acids, which define a sequence that by itself, or as part of a larger sequence, binds to an antibody generated in response to such sequence. An epitope is not limited to a polypeptide having a sequence identical to the portion of the parent protein from which it is derived. Indeed, viral genomes are in a state of constant change and exhibit relatively high degrees of variability between isolates. Thus the term "epitope" encompasses sequences identical to the native sequence, as well as modifications, such as deletions, substitutions and/or insertions to the native sequence. Generally, such modifications are conservative in nature but non-conservative modifications are also contemplated. The term specifically includes "mimotopes," i.e. sequences that do not identify a continuous linear native sequence or do not necessarily occur in a native protein, but functionally mimic an epitope on a native protein. The term "epitope" specifically includes linear and conformational epitopes.

The term "vector" is used to refer to a rDNA molecule capable of autonomous replication in a cell and to which a DNA segment, e.g., gene or polynucleotide, can be operatively linked so as to bring about replication of the attached segment. Vectors capable of directing the expression of genes encoding for one or more polypeptides are referred to herein as "expression vectors." The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

A "phage display library" is a protein expression library that expresses a collection of cloned protein sequences as fusions with a phage coat protein. Thus, the phrase "phage display library" refers herein to a collection of phage (e.g., filamentous phage) wherein the phage express an external (typically heterologous) protein. The external protein is free to interact with (bind to) other moieties with which the phage are contacted. Each phage displaying an external protein is a "member" of the phage display library.

The term "filamentous phage" refers to a viral particle capable Of displaying a heterogenous polypeptide on its surface, and includes, without limitation, fl, fd, Pfl, and M13. The filamentous phage may contain a selectable marker such as tetracycline (e.g., "fd-tet"). Various filamentous phage display systems are well known to those of skill in the art (see, e.g., Zacher et al. *Gene* 9: 127-140 (1980), Smith et al. *Science* 228: 1315-1317 (1985); and Parmley and Smith *Gene* 73: 305-318 (1988)).

The term "panning" is used to refer to the multiple rounds of screening process in identification and isolation of phages carrying compounds, such as antibodies, with high affinity and specificity to a target.

B. Detailed Description

Techniques for performing the methods of the present invention are well known in the art and described in standard laboratory textbooks, including, for example, Ausubel et al., *Current Protocols of Molecular Biology*, John Wiley and Sons (1997); *Molecular Cloning: A Laboratory Manual*, Third Edition, J. Sambrook and D. W. Russell, eds., Cold Spring Harbor, N.Y., USA, Cold Spring Harbor Laboratory Press, 2001; O'Brian et al., *Analytical Chemistry of Bacillus Thuringiensis*, Hickle and Fitch, eds., Am. Chem. Soc., 1990; *Bacillus thuringiensis: biology, ecology and safety*, T. R. Glare and M. O'Callaghan, eds., John Wiley, 2000; *Antibody Phage Display, Methods and Protocols*, Humana Press, 2001; and *Antibodies*, G. Subramanian, ed., Kluwer Academic, 2004. Mutagenesis can, for example, be performed using site-directed mutagenesis (Kunkel et al., *Proc. Natl. Acad. Sci USA* 82:488-492 (1985)). PCR amplification methods are described in U.S. Pat. Nos. 4,683,192, 4,683,202, 4,800,159, and 4,965,188, and in several textbooks including "PCR Technology: Principles and Applications for DNA Amplification", H. Erlich, ed., Stockton Press, New York (1989); and *PCR Protocols: A Guide to Methods and Applications*, Innis et al., eds., Academic Press, San Diego, Calif. (1990).

The present invention concerns constructs and libraries comprising antibody surrogate light chain sequences.

Surrogate Light Chain Constructs

As discussed above, pre-B cells have been identified in the bone marrow as lymphocytes that produce µ heavy chains but instead of the fully developed light chains express a set of B lineage-specific genes called VpreB(1-3) and λ5, respectively. The VpreB and λ5 polypeptides together form a non-covalently associated, Ig light chain-like structure, which is called the surrogate light chain. The surrogate light chain, although not an antibody chain, naturally associates with all antibody heavy chains, and surrogate light chain-antibody heavy chain complexes have been shown to bind self-antigens.

In one aspect, the present invention provides polypeptides comprising VpreB and/or λ5 sequences and having the ability to bind a target. The target can be any peptide or polypeptide that is a binding partner for the VpreB and/or λ5 sequence-containing polypeptides of the present invention. Targets specifically include all types of targets generally referred to as "antigens" in the context of antibody binding.

Thus, the polypeptides of the present invention include, without limitation, conjugates of VpreB sequences to heterogeneous amino acid sequences, provided that they retain the ability to bind a desired target. The binding of the VpreB sequence to the heterogeneous amino acid sequence can be either covalent or non-covalent, and may occur directly, or through a linker, including peptide linkers.

Specific examples of the polypeptide constructs herein include polypeptides in which a VpreB sequence, such as a VpreB1, VpreB2, or VpreB3 sequence, including fragments and variants of the native sequences, is conjugated to a λ5 sequence, including fragments and variants of the native sequence. Representative fusions of this type are illustrated in FIGS. 2 and 11 and described in the Examples.

In a direct fusion, typically the C-terminus of a VpreB sequence (e.g. a VpreB1, VpreB2 or VpreB3 sequence) is fused to the N-terminus of a λ5 sequence. While it is possible to fuse the entire length of a native VpreB sequence to a full-length λ5 sequence (see, e.g. the first diagram in FIG. 3), typically the fusion takes place at or around a CDR3 analogous site in each of the-two polypeptides. Such CDR3 analogous sites for VpreB1 and λ5 are illustrated in FIG. 1, and a representative fusion construct is illustrated in FIG. 2. In this embodiment, the fusion may take place within, or at a location within about 10 amino acid residues at either side of the CDR3 analogous region. In a preferred embodiment, the fusion takes place between about amino acid residues 116-126 of the native human VpreB1 sequence (SEQ ID NO: 1) and between about amino acid residues 82 and 93 of the native human λ5 sequence (SEQ ID NO: 5).

Figure 3:
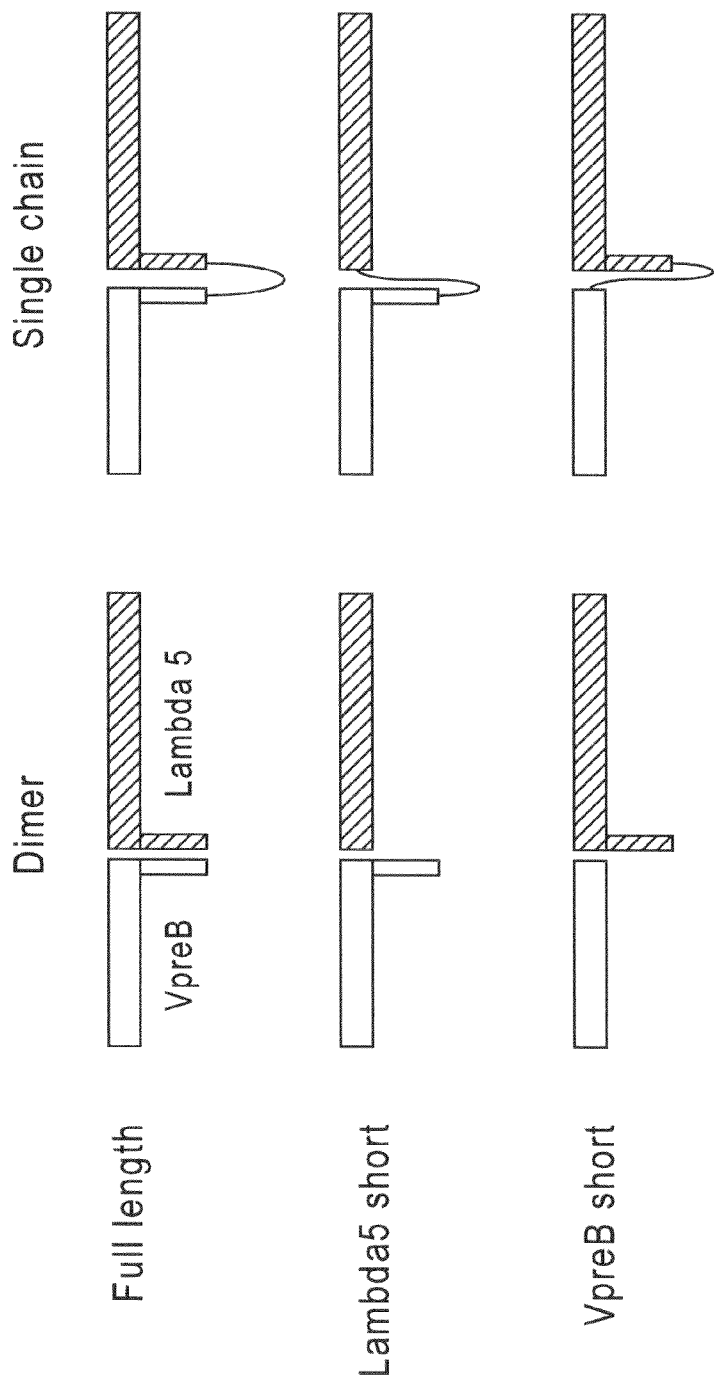
FIG. 3 is a schematic illustration of various surrogate light chain deletion and single chain constructs.
Figure 4:
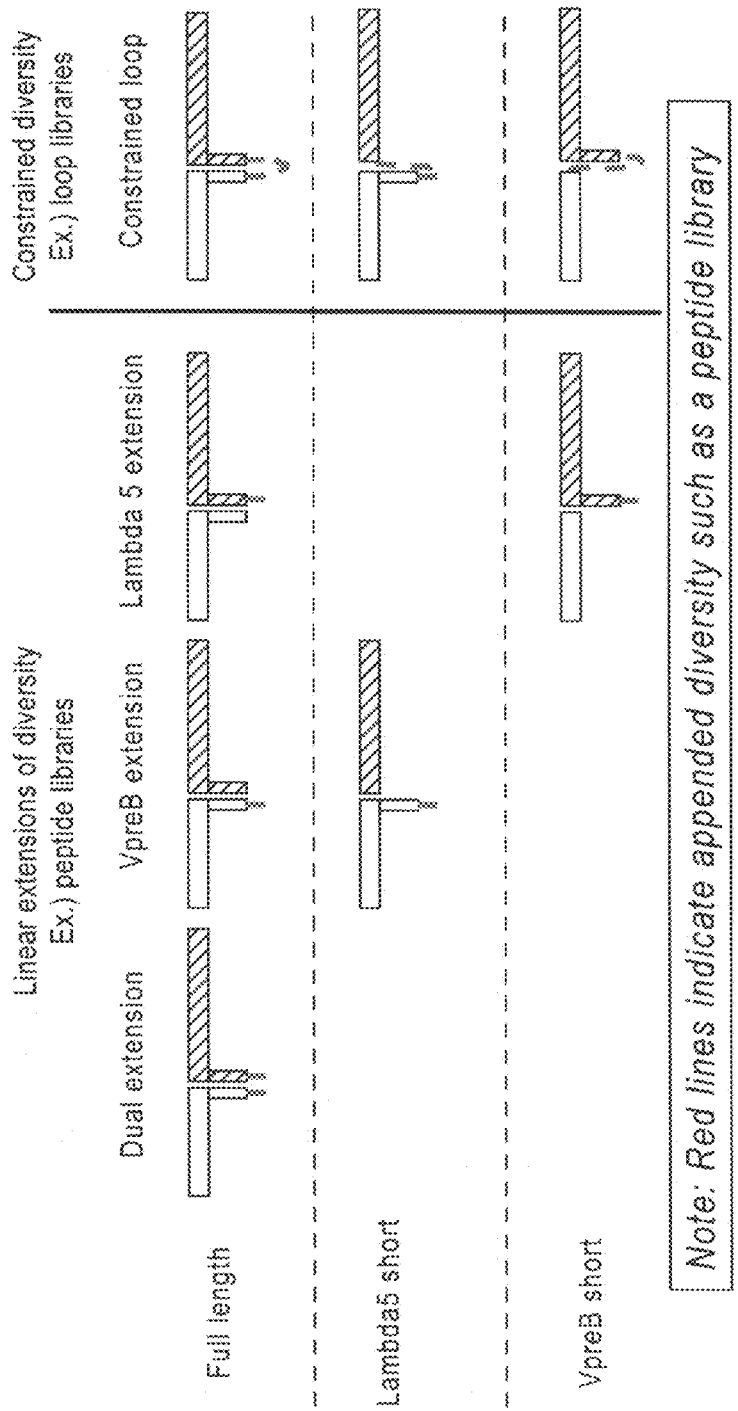
FIG. 4 schematically illustrates the incorporation of combinatorial functional diversity into surrogate light chain constructs.

It is also possible to fuse the VpreB sequence to the CDR3 region of an antibody λ light chain, as shown in FIG. 2. Further constructs, in which only one of VpreB and λ5 is truncated are shown in FIG. 3. Similar constructs can be prepared using antibody κ light chain sequences.

Further direct fusion structures are illustrated on the right side of FIG. 11. The structure designated "SLC fusion 1" is a tetramer, composed of two dimers, in which the fusion of a truncated V-preB1 sequence (lacking the characteristic "tail" at the C-terminus of native VpreB I) to a similarly truncated λ5 sequence is non-covalently associated with an antibody heavy chain. The structure designated "SLC fusion 2" is a tetramer, composed of two dimers, in which the fusion of a truncated VpreB1 sequence (lacking the characteristic "tail" at the C-terminus of native VpreB1) to an antibody light chain constant region is non-covalently associated with an antibody heavy chain. The structure designated "SLC fusion 3" is a tetramer, composed of two dimers, in which the fusion of an antibody light chain variable region to a truncated λ5 sequence (lacking the characteristic "tail" at the N-terminus of native λ5) is non-covalently associated with an antibody heavy chain.

As noted above, in addition to direct fusions, the polypeptide constructs of the present invention include non-covalent associations of a VpreB sequence (including fragments and variants of a native sequence) with a heterogeneous sequence, such as a λ5 sequence (including fragments and variants of the native sequence), and/or an antibody sequence. Thus, for example, a full-length VpreB sequence may be non-covalently associated with a truncated λ5 sequence. Alternatively, a truncated VpreB sequence may be non-covalently associated with a full-length λ5 sequence.

Surrogate light chain constructs comprising non-covalently associated VpreB1 and λ5 sequences, in non-covalent association with an antibody heavy chain, are shown on the left side of FIG. 11. As the various illustrations show, the structures may include, for example, full-length VpreB1 and λ5 sequences, a full-length VpreB1 sequence associated with a truncated λ5 sequence ("Lambda 5dT"), a truncated V-preB1 sequence associated with a full-length λ5 sequence (VpreB dT") and a truncated VpreB1 sequence associated with a truncated λ5 sequence ("Short").

Although FIG. 11 illustrates certain specific constructs, one of ordinary skill will appreciate that a variety of other constructs can be made and used in a similar fashion. For example, the structures can be asymmetrical, comprising different surrogate light chain sequences in each arm, and/or having trimeric or pentameric structures, as opposed to the structures illustrated in FIG. 11. It is also possible to include different functionalities in various portions of the surrogate light chain constructs of the present invention, thereby producing multi-specific and/or multivalent constructs.

If desired, the constructs of the present invention can be engineered, for example, by incorporating or appending known sequences or sequence motifs from the CDR1, CDR2 and/or CDR3 regions of antibodies, including known therapeutic antibodies into the CDR1, CDR2 and/or CDR3 analogous regions of the surrogate light chain sequences. This allows the creation of molecules that are not antibodies, but will exhibit binding specificities and affinities very similar to those of a known therapeutic antibody.

Figure 5:
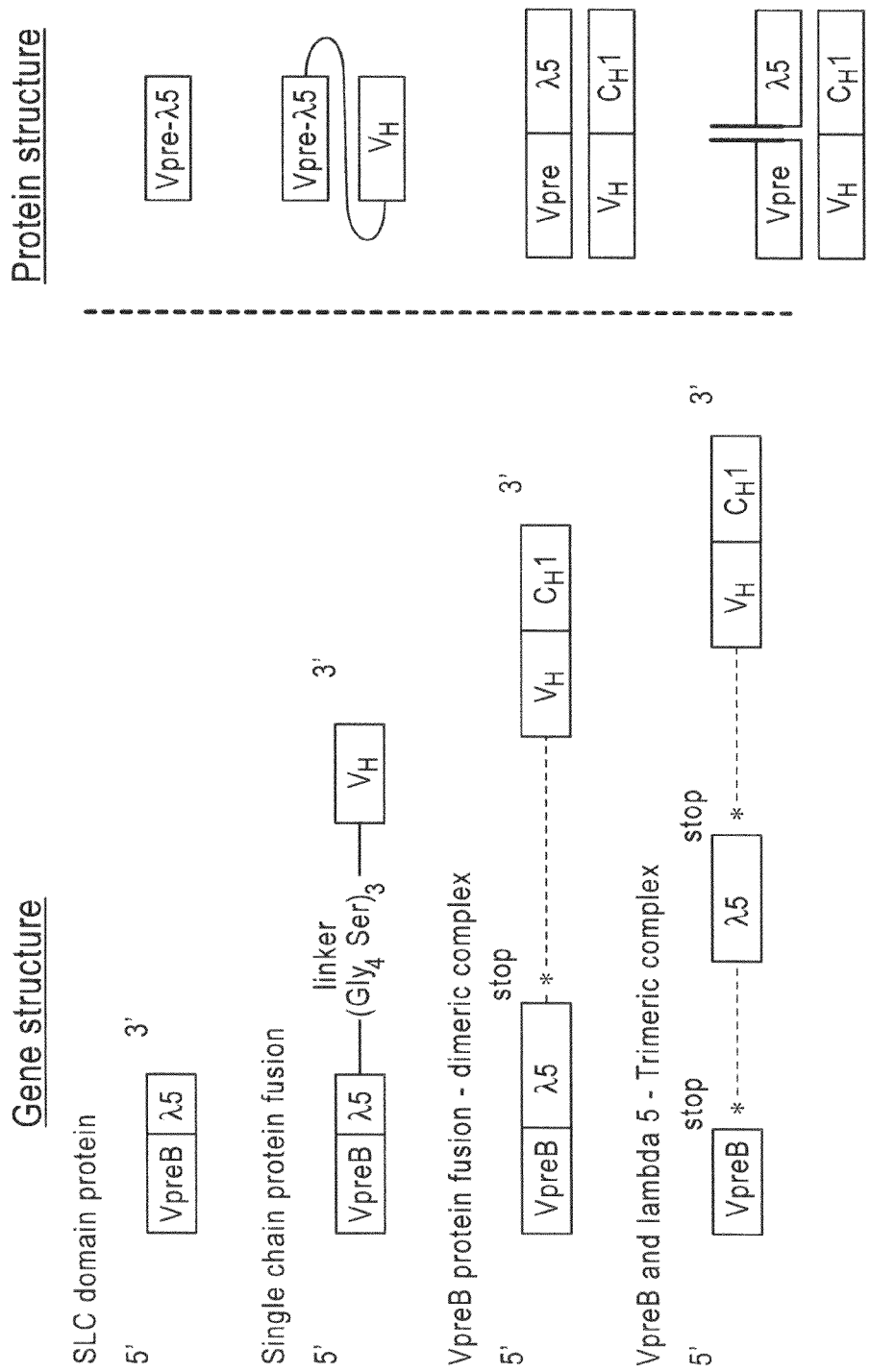
FIG. 5 shows the gene and protein structures of various illustrative surrogate light chain constructs.
Figure 7:
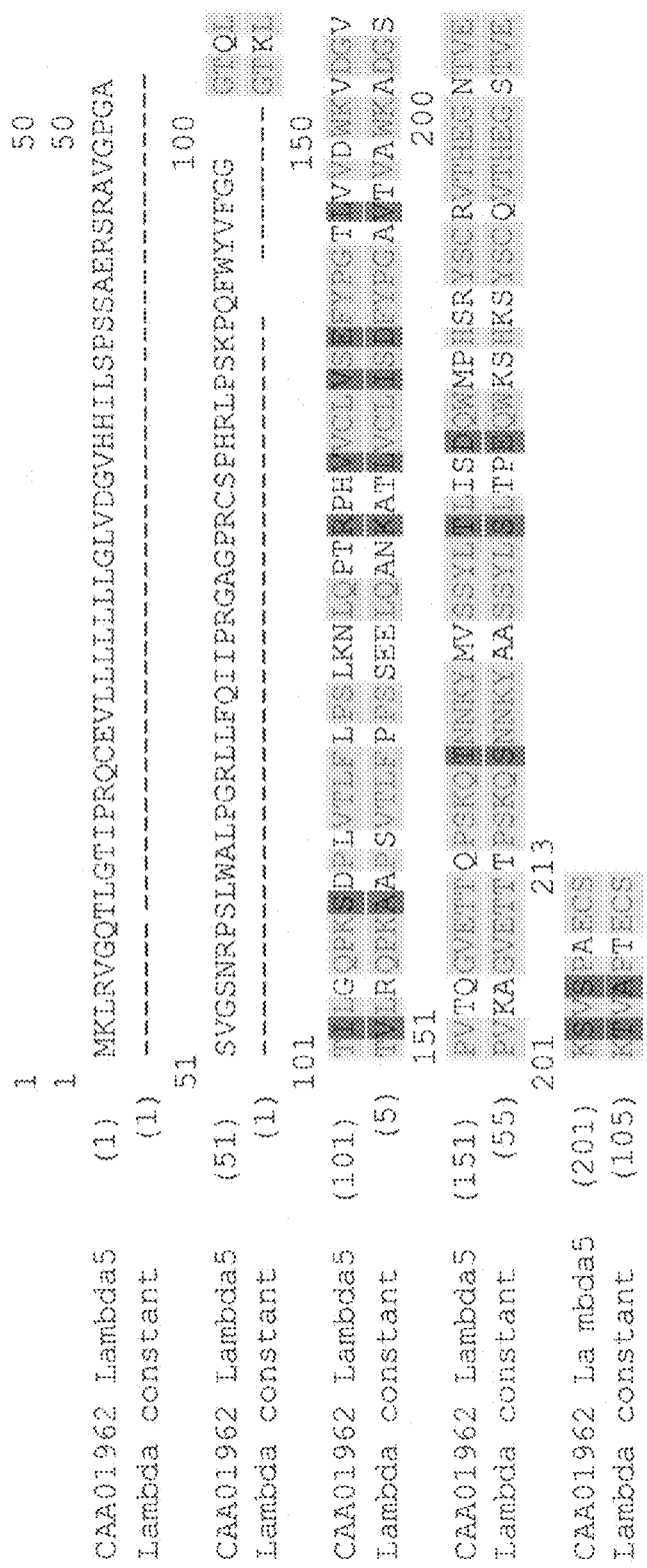
FIG. 7 is the alignment of a λ5 sequence (SEQ ID NO: 5) with an antibody λ light chain constant region sequence (SEQ ID NO: 32). As shown in the figure, the aligned λ sequence shows only 62% (amino acids 97 to 209) sequence identity to the corresponding antibody λ light chain constant region sequences.

All surrogate light chain constructs herein may be associated with antibody sequences. For example, as shown in FIG. 5, a VpreB-λ5 fusion can be linked to an antibody heavy chain variable region sequence by a peptide linker. In another embodiment, a VpreB-λ5 fusion is non-covalently associated with an antibody heavy chain, or a fragment thereof including a variable region sequence to form a dimeric complex. In yet another embodiment, the VpreB and λ5 sequences are non-covalently associated with each other and an antibody heavy chain, or a fragment thereof including a variable region sequence, thereby forming a trimeric complex. Exemplary constructs comprising an antibody heavy chain are illustrated in FIG. 1.

While the constructs of the present invention are illustrated by reference to certain embodiments, one of ordinary skill will understand that numerous further embodiments obtained by various permutations of surrogate light chain and antibody sequences are possible, and are within the scope of the present invention. The present invention includes all constructs that comprise surrogate light chain sequences and have the ability to bind a desired target. In certain embodiment, the constructs also have the ability to associate with antibody heavy chain variable region sequences.

The constructs of the present invention may be used to build libraries of surrogate light chain sequences, which can be used for various purposes, similarly to antibody libraries, including selection of constructs with the desired binding specificities and affinities.

When the VpreB and λ5 surrogate light chain sequences are non-covalently associated with each other, the free ends of one or both components (i.e. the C-terminal end of the VpreB sequence and/or the N-terminal end of the λ5 sequence) are available for incorporating an additional diversity into the library of such sequences. For instance, a random peptide library can be appended or substituted to one of these free ends and panned for specific binding to a particular target. By combining the surrogate light chain identified to have the desired binding specificity with a heavy chain or heavy chain fragment from an antibody to the same target, a molecule can be created that has the ability to bind to the cognate target on two distinct places. This tandem binding, or "chelating" effect, strongly reinforces the binding to a single target, similarly to the avidity effects seen in dimeric immunoglobulins. It is also possible to use components binding to different targets. Thus, for example, the surrogate light chain component with the desired binding specificity can be combined with an antibody heavy chain or heavy fragment binding to a different target. For instance, the surrogate light chain component may bind a tumor antigen while the antibody heavy chain or heavy chain fragment may bind to effector cells. This way, a single entity with targeting and anti-tumor activity can be created. In a particular embodiment, the appendage or the polypeptide that connects the VpreB and λ5 sequences can be an antibody or antibody fragments, such as a Fab or a scFv fragment. The incorporation of an antibody sequence will not only create a "chelating" effect but can also generate bispecificity in a single molecule, without the need of a second independent arm, such as that found in bispecific antibodies. The two specificities may be to different parts of the same target, to disparate targets, or to a target antibody complex. Similarly, multi-specific constructs can be made with any type of molecule, other than antibodies or antibody fragments, including peptides, proteins, enzymes, and the like. For example, the surrogate light chain component with the desired specificity can be combined with any therapeutic peptide or protein.

Preparation of Surrogate Light Chain Constructs

The surrogate light chain constructs of the present invention can be prepared by methods known in the art, including well known techniques of recombinant DNA technology.

Nucleic acid encoding surrogate light chain, e.g. VpreB and λ5 polypeptides, can be isolated from natural sources, e.g. developing B cells and/or obtained by synthetic or semi-synthetic methods. Once this DNA has been identified and isolated or otherwise produced, it can be ligated into a replicable vector for further cloning or for expression.

Cloning and expression vectors that can be used for expressing the coding sequences of the polypeptides herein are well known in the art and are commercially available. The vector components generally include, but are not limited to, one or more of the following: a signal sequence, an origin of replication, one or more marker genes, an enhancer element, a promoter, and a transcription termination sequence. Suitable host cells for cloning or expressing the DNA encoding the surrogate light chain constructs in the vectors herein are prokaryote, yeast, or higher eukaryote (mammalian) cells, mammalian cells are being preferred.

Examples of suitable mammalian host cell lines include, without limitation, monkey kidney CV1 line transformed by SV40 (COS-7, ATCC CRL 1651); human embryonic kidney line 293 (293 cells) subcloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hop G2).

For use in mammalian cells, the control functions on the expression vectors are often provided by viral material. Thus, commonly used promoters can be derived from the genomes of polyoma, Adenovirus2, retroviruses, cytomegalovirus, and Simian Virus 40 (SV40). Other promoters, such as the β-actin protomer, originate from heterologous sources. Examples of suitable promoters include, without limitation, the early and late promoters of SV40 virus (Fiers et al., *Nature,* 273: 113 (1978)), the immediate early promoter of the human cytomegalovirus (Greenaway et al., *Gene,* 18: 355-360 (1982)), and promoter and/or control sequences normally associated with the desired gene sequence, provided such control sequences are compatible with the host cell system.

Transcription of a DNA encoding a desired heterologous polypeptide by higher eukaryotes is increased by inserting an enhancer sequence into the vector. The enhancer is a cis-acting element of DNA, usually about from 10 to 300 bp, that acts on a promoter to enhance its transcription-initiation activity. Enhancers are relatively orientation and position independent, but preferably are located upstream of the promoter sequence present in the expression vector. The enhancer might originate from the same source as the promoter, such as, for example, from a eukaryotic cell virus, e.g. the SV40 enhancer on the late side of the replication origin (bp 100-270), the cytomegalovirus early promoter enhancer, the polyoma enhancer on the late side of the replication origin, and adenovirus enhancers.

Expression vectors used in mammalian host cells also contain polyadenylation sites, such as those derived from viruses such as, e.g., the SV40 (early and late) or HBV.

An origin of replication may be provided either by construction of the vector to include an exogenous origin, such as may be derived from SV40 or other viral (e.g., Polyoma, Adeno, VSV, BPV) source, or may be provided by the host cell.

The expression vectors usually contain a selectable marker that encodes a protein necessary for the survival or growth of a host cell transformed with the vector. Examples of suitable selectable markers for mammalian cells include dihydrofolate reductase (DHFR), thymidine kinase (TK), and neomycin.

Suitable mammalian expression vectors are well known in the art and commercially available. Thus, for example, the surrogate light chain constructs of the present invention can be produced in mammalian host cells using a pCl expression vector (Promega), carrying the human cytomegalovirus (CMV) immediate-early enhancer/promoter region to promote constitutive expression of a DNA insert. The vector can contain a neomycin phosphotransferase gene as a selectable marker.

The surrogate light chain constructs of the present invention can also be produced in bacterial host cells. Control elements for use in bacterial systems include promoters, optionally containing operator sequences, and ribosome binding sites. Suitable promoters include, without limitation, galactose (gal), lactose (lac), maltose, tryptophan (trp), β-lactamase promoters, bacteriophage λ and T7 promoters. In addition, synthetic promoters can be used, such as the tac promoter. Promoters for use in bacterial systems also generally contain a Shine-Dalgarno (SD) sequence operably linked to the DNA encoding the Fab molecule. The origin of replication from the plasinid pBR322 is suitable for most Gram-negative bacteria.

The coding sequences of the individual chains within a multi-chain construct comprising antibody surrogate light chain sequences can be present in the same expression vector, under control of separate regulatory sequences, or in separate expression vectors, used to cotransfect a desired host cells, including eukaryotic and prokaryotic hosts. Thus, multiple genes can be coexpressed using the Duet™ vectors commercially available from Novagen.

The transformed host cells may be cultured in a variety of media. Commercially available media for culturing mammalian host cells include Ham's F10 (Sigma), Minimal Essential Medium ((MEM), (Sigma), RPMI-1640 (Sigma), and Dulbecco's Modified Eagle's Medium ((DMEM), Sigma). In addition, any of the media described in Ham et al., *Meth. Enz.* 58:44 (1979) and Barnes et al., *Anal. Biochem.* 102:255 (1980) may be used as culture media for the host cells. The culture conditions, such as temperature, pH, and the like, are those previously used with the host cell selected for expression, and are included in the manufacturer's instructions or will otherwise be apparent to the ordinarily skilled artisan.

Further suitable media for culturing mammalian, bacterial (e.g. *E. coli*) or other host cells are also described in standard textbooks, such as, for example, Sambrook et al., supra, or Ausubel et al., supra.

Purification can be performed by methods known in the art. In a preferred embodiment, the surrogate antibody molecules are purified in a 6× His-tagged form, using the Ni-NTA purification system (Invitrogen).

Libraries Comprise Surrogate Light Chain Sequences

The present invention further concerns various libraries of surrogate light chain sequences and constructs comprising such sequences. Thus, such libraries may comprise, consist essentially of, or consist of, displays of surrogate light chain sequences, such as the VpreB- and/or λ5-containing constructs of the present invention, including, without limitation, those specifically described above, illustrated in the figures and/or described in the Examples.

The libraries of the present invention are preferably in the form of a display. Systems for displaying heterologous proteins, including antibodies and other polypeptides, are well known in the art. Antibody fragments have been displayed on the surface of filamentous phage that encode the antibody genes (Hoogenboom and Winters *J. Mol. Biol.*, 222:381 388 (1992); McCafferty et al., *Nature* 348(6301):552 554 (1990); Griffiths et al. *EMBO J.*, 13(14):3245-3260 (1994)). For a review of techniques for selecting and screening antibody libraries see, e.g., Hoogenboom, *Nature Biotechnol.* 23(9): 1105-1116 (2005). In addition, there are systems known in the art for display of heterologous proteins and fragments thereof on the surface of *Escherichia coli* (Agterberg et al., *Gene* 88:37-45 (1990); Charbit et al., *Gene* 70:181-189 (1988); Francisco et al., *Proc. Natl. Acad. Sci. USA* 89:2713-2717 (1992)), and yeast, such as *Saccharomyces cerevisiae* (Boder and Wittrup, *Nat. Biotechnol.* 15:553-557 (1997); Kieke et al., *Protein Eng.* 10: 1303-1310 (1997)). Other known display techniques include ribosome or mRNA display (Mattheakis et al., *Proc. Natl. Acad. Sci. USA* 91:9022-9026 (1994); Hanes and Pluckthun, *Proc. Natl. Acad. Sci. USA* 94:4937-4942 (1997)), DNA display (Yonezawa et al., *Nucl. Acid Res.* 31(19):e118 (2003)); microbial cell display, such as bacterial display (Georgiou et al., *Nature Biotech.* 15:29-34 (1997)), display on mammalian cells, spore display (Isticato et al., *J. Bacteriol.* 183:6294-6301 (2001); Cheng et al., *Appl. Environ. Microbiol.* 71:3337-3341 (2005) and co-pending provisional application Ser. No. 60/865,574, filed Nov. 13, 2006), viral display, such as retroviral display (Urban et al., *Nucleic Acid Res.* 33:e35 (2005), display based on protein-DNA linkage (Odegrip et al., *Proc. Acad. Natl. Sci. USA* 101:2806-2810 (2004); Reiersen et al., *Nucleic Acids Res.* 33:e10 (2005)), and microbead display (Sepp et al., *FEBS Lett.* 532:455-458 (2002)).

For the purpose of the present invention, the surrogate light chain-containing libraries may be advantageously displayed using any display technique, including phage display and spore display.

In phage display, the heterologous protein, such as a surrogate light chain polypeptide, is linked to a coat protein of a phage particle, while the DNA sequence from which it was expressed is packaged within the phage coat. Details of the phage display methods can be found, for example, McCafferty et al., *Nature* 348, 552-553 (1990)), describing the production of human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell.

Phage display can be performed in a variety of formats; for their review see, e.g. Johnson, Kevin S. and Chiswell, David J., *Current Opinion in Structural Biology* 3, 564-571 (1993). Several sources of heavy chain V-gene segments can be discovered through phage display. Clarkson et al., *Nature* 352, 624-628 (1991) isolated a diverse array of anti-oxazolone heavy chains and light chains from a small random combinatorial library of V genes derived from the spleens of immunized mice. A repertoire of heavy and light chain V genes from unimmunized human donors can be constructed and recovered specific to a diverse array of antigens (including self-antigens) essentially following the techniques described by Marks et al., *J. Mol. Biol.* 222, 581-597 (1991), or Griffith et al., *EMBO J.* 12, 725-734 (1993). These and other techniques known in the art, can be adapted to the display of any polypeptide, including polypeptides and other constructs comprising surrogate light chain sequences. Thus, for example, the surrogate light chain can be supplemented with a collection of heavy chains from either a naturally diverse source, such as lymphocytes, or a synthetically generated collection created entirely through techniques of molecular biology. These collections can be cloned, expressed and selected, by methods known in the art. The selected resulting SURROBODY™ can be used directly, expressed as multimeric a molecule, or further optimized through heavy chain optimization, or surrogate light chain optimization, for example, using random or nonrandom site specific or regional mutagenesis.

Spore display systems are based on attaching the sequences to be displayed to a coat protein, such as a *Bacillus subtilis* spore coat protein. The spore protoplast (core) is surrounded by the cell wall, the cortex, and the spore coat. Depending on the species, an exosporium may also be present. The core wall is composed of the same type of peptidoglycan as the vegetative cell wall. Spore display, including surface display system using a component of the *Bacillus subtilis* spore coat (CorB) and *Bacillus thuringiensis* (Bt) spore display, is described in Isticato et al., *J. Bacteriol.* 183:6294-6301 (2001); Cheng et al., *Appl. Environ. Microbiol.* 71:3337-3341 (2005), the entire disclosures of which is hereby expressly incorporated by reference. Various spore display techniques are also disclosed in U.S. Patent Application Publication Nos. 20020150594; 20030165538; 20040180348; 20040171065; and 20040254364, the entire disclosures are hereby expressly incorporated by reference herein.

An advantage of spore display systems is the homogenous particle surface and particle size of non-eukaryotic nature, which is expected to provide an ideal non-reactive background. In addition, the particle size of spores is sufficient to enable selection by flow cytometry that permits selectable clonal isolation, based upon interactions.

Leveraging on the stability of spores, it is possible to perform various post-sporulation chemical, enzymatic and/or environmental treatments and modification. Thus, it is possible to stabilize structural helical structures with chemical treatment using trifluoroethanol (TFE), when such structures are displayed. In addition, oxidative stress treatments, such as treatments with Reactive Oxygen Species (e.g. peroxide) or reactive Nitrogen Species (e.g. nitrous acid) are possible. It is also possible to expose defined or crude populations of spore-displayed polypeptides to enzymatic treatments, such as proteolytic exposure, other enzymatic processes, phosphorylation, etc. Other possible treatments include, without limitation, nitrosylation by peroxynitrite treatment, proteolysis by recombinant, purified, or serum protease treatment, irradiation, coincubation with known chaperones, such as heat shock proteins (both bacterial and mammalian), treatment with folding proteins, such as protein disulfide isomerase, prolyl isomerase, etc., lyophilization, and preservative-like treatments, such as treatment with thimerosol. These treatments can be performed by methods well known in the art.

Similar techniques can be used in all spore display systems, including displays where the attachment is to a spore coat protein, including, for example, the spore display systems disclosed in Uses of Surrogate Light Chain Sequences, Constructs and Libraries Containing Same The libraries of the present invention can be used to identify surrogate light chain sequences and surrogate light chain constructs, such as fusions comprising surrogate light chain sequences, with desired properties. For example, in vitro or in vivo screening of the libraries herein can yield polypeptides comprising surrogate light chain sequences binding to desired targets with high binding specificity and affinity. Thus, the libraries herein can be used to identify molecules for therapeutic and diagnostic purposes, such as polypeptides comprising surrogate light chain sequences that bind to tumor markers or other molecular targets of therapeutic intervention. In addition, by the techniques described above, highly diverse libraries of surrogate light chain polypeptides can be engineered, including libraries comprising a collection of polypeptides binding to the same target, libraries of polypeptides binding to different targets, libraries of polypeptides with multiple specificities, and the like.

As a result of their ability to bind to any desired target, the antibody surrogate light chain constructs of the present invention can be used in analytical and diagnostic assays, to detect the presence of a desired target molecule, such as a tumor antigen or any polypeptide associated with a disease state or condition. In addition, the surrogate light chain constructs of the present invention can be used as therapeutic agents, such as, for example, in cancer therapy, to target tumor antigens that have been determined to associate with the development and/or spread of cancer.

Further details of the invention are provided in the following non-limiting Examples.

EXAMPLE 1

VpreB as a Binding Domain Protein and Fusions Containing It

To make a VpreB binding domain a single protein shown in FIG. 5 is created recombinantly. The SLC binding domain protein construct is comprised of the amino acids 20 to 121 from VpreB1 and the amino acids 87 to 105 from λ5. If desired, to create novel and specific binding capabilities, the molecule is reengineered according to structural or sequence evidence. Additionally, or alternatively, a collection of variants is created either randomly, for example by error-prone PCR, or directly by single or multi-site specific mutagenesis with a collection of amino acids. The resulting clones or collections are then cloned in frame with pIII for use in phage or phagemid display. This phagemid construct is transformed into TG1 cells. Next a single colony is propagated in Luria Broth (LB) supplemented with 50 μg/ml Ampicillin and 2% glucose until it reached OD600 ~0.3, and infected with MK307 helper phage at 37° C. for 30 minutes without shaking. The cells are then pelleted and then resuspended in LB containing 50 μg/ml ampicillin and 75 μg/ml kanamycin and allowed to grow overnight with vigorous aeration at 30° C. The next day the supernatant containing phagemid expressed SLC-HC fusion protein is used in Phage ELISA to determine targeted binding. Briefly the ELISA entails coating and blocking of an ELISA plate with human TNF-α, followed by incubation of the SLC-HC phage for 2 hours at 4° C., washing with PBS-Tween-20 (0.05%) and direct detection with anti-m13-HRP antibody. Alternatively binding is assessed by directly amplifying or eluting the bound phage and determining phage titers using XL-1Blue cells. This example describes a SLC binding domain fusion as a single clone, but this SLC can be recombinantly recombined with other heterologous sequences that recognize a common target and screened as a library. Furthermore, this SLC binding protein can be combined with a previously selected collection of heavy chains and screened directly on the same target of interest or a second target of interest to create a bispecific molecule. Alternatively this reinforced binding or bispecific binding can be discovered by screening in conjunction with unselected collections of heavy chains. In addition, while this example refers to antibody heavy chains, it should be understood that a complete heavy chain is not needed. Single-chain fusions comprising heavy chain variable region sequences, in the absence of a heavy chain constant region, or a complete heavy chain constant region, can be made in an analogous manner and are within the scope of this example.

EXAMPLE 2

VpreB Fusions as a Variable Heavy Chain (VH) Partner

A functional VpreB-λ5 fusion protein shown in the second diagram of FIG. 5 (designated "VpreB protein fusion—dimeric complex") is recombinantly created. The VpreB-λ5 fusion protein is comprised of an m13 gene III signal sequence, the amino acids 20 to 115 from VpreB1, and the amino acids 83 to 209 from λ5. This construct is coexpressed with a variable heavy chain-CH1 fusion in frame with pIII for use in phage or phagemid display. As a VH coding sequence the VH coding sequence from the anti-TNF-α antibody, D2E7, is used, and CH1 is the CH1 region of human IgG1. This phagemid construct is transformed into TG1 cells. Next, a single colony is propagated in Luria Broth (LB) supplemented with 50 μg/ml Ampicillin and 2% glucose until it reached OD600 ~0.3, and infected with MK307 helper phage at 37 degrees for 30 minutes, without shaking. The cells are then pelleted and then resuspended in LB containing 50 μg/ml ampicillin and 75 μg/ml kanamycin and allowed to grow overnight with vigorous aeration at 30 degrees. The next day the supernatant containing phagemid expressed SLC-HC fusion protein is used in Phage ELISA to determine targeted binding. Briefly the ELISA entails coating and blocking of an ELISA plate with human TNF-α, followed by incubation of the SLC-HC phage for 2 hours at 4 degrees, washing with PBS-Tween-20 (0.05%) and direct detection with anti-m13-HRP antibody. Alternatively binding can be assessed by directly amplifying or eluting the bound phage and determining phage titers using XL-1Blue cells. This example describes a SLC fusion partnered with a heavy chain variable-CH1 fusion as a single clone, but this SLC can also be combined with a focused collection of heavy chain variable regions that recognize a common target and screened as a library. Furthermore, this SLC fusion can be combined with an unselected collection of heavy chains and screened directly on a target of interest. As a reasonable SLC fusion alternative, VH association can be reinforced by fusing the constant lambda region from a traditional antibody light chain instead of the λ5 protein fragment.

EXAMPLE 3

VpreB and Lambda5 as an Associated Variable Heavy Chain (VH) Partner

The VpreB-λ5 coexpressed protein shown in the third diagram of FIG. 5 (designated "VpreB and lambda 5—trimeric complex") is made of an m13 gene III signal sequence and the corresponding amino acids of the predicted mature, processed VpreB1 (amino acids 20 to 146) and lambda 5 (amino acids 31 to 209). These are coexpressed with a variable heavy chain-CH1 fusion in frame with pIII for use in phage or phagemid display. As a VH coding sequence the VH coding sequence from the anti-TNF-α antibody, D2E7, is used, and CH1 is the CH1 region from human IgG1. This phagemid construct is transformed into TG1 cells. Next a single colony is propagated in Luria Broth (LB) supplemented with 50 μg/ml Ampicillin and 2% glucose until it reached OD600 ~0.3, and is then infected with MK307 helper phage at 37 degrees for 30 minutes, without shaking. The cells are then pelleted and then resuspended in LB containing 50 µg/ml ampicillin and 75 µ/ml kanamycin and allowed to grow overnight with vigorous aeration at 30 degrees. The next day the supernatant containing phagemid expressed SLC HC trimeric protein complexes is used in Phage ELISA to determine targeted binding. Briefly the ELISA entails coating and blocking of an ELISA plate with human TNF-α, followed by incubation of the SLC-HC phage for 2 hours at 4 degrees, washing with PBS-Tween-20 (0.05%) and direct detection with anti-m13-HRP antibody. Alternatively binding can be assessed by directly amplifying or eluting the bound phage and determining phage titers using XL-1Blue cells. This example describes a SLC partnered with a heavy chain variable-CH1 fusion as a single clone, but this SLC can be combined with a focused collection of heavy chain variable regions that recognize a common target and screened as a library. Furthermore, this SLC fusion can be combined with an unselected collection of heavy chains and screened directly on a target of interest.

EXAMPLE 4

Engineering Diversity into VpreB1 CDR3 Analogous Regions

As the CDR analogous regions of the surrogate light chain (SLC) will have similar functions to the CDR's of an antibody light chain, it is important to determine the fusion points between the VpreB and λ5. According to one approach the most suitable fusion point for a particular purpose is determined starting with the CDR3 analogous site containing all VpreB amino acids and incrementally substituting amino acids position by position from λ5 encoded in clonable oligonucleotides. This incremental substitution continues until the CDR analogous site is entirely composed of a λ5 source sequence. At some point during this process, it might be desirable to add a complementary heavy chain and allow/facilitate its antigen binding and recognition. To further enhance or enable this complementation random diversity can be used in any of the CDR analogous sites, as well as diversity based upon matched CDR length analysis. Alternatively, or in addition, antibody Vλ5 sequences can be used to add diversity, as their CDR lengths match well with VpreB CDR analogous site lengths.

EXAMPLE 5

Adding Functionalities to SLC Components

Figure 9:
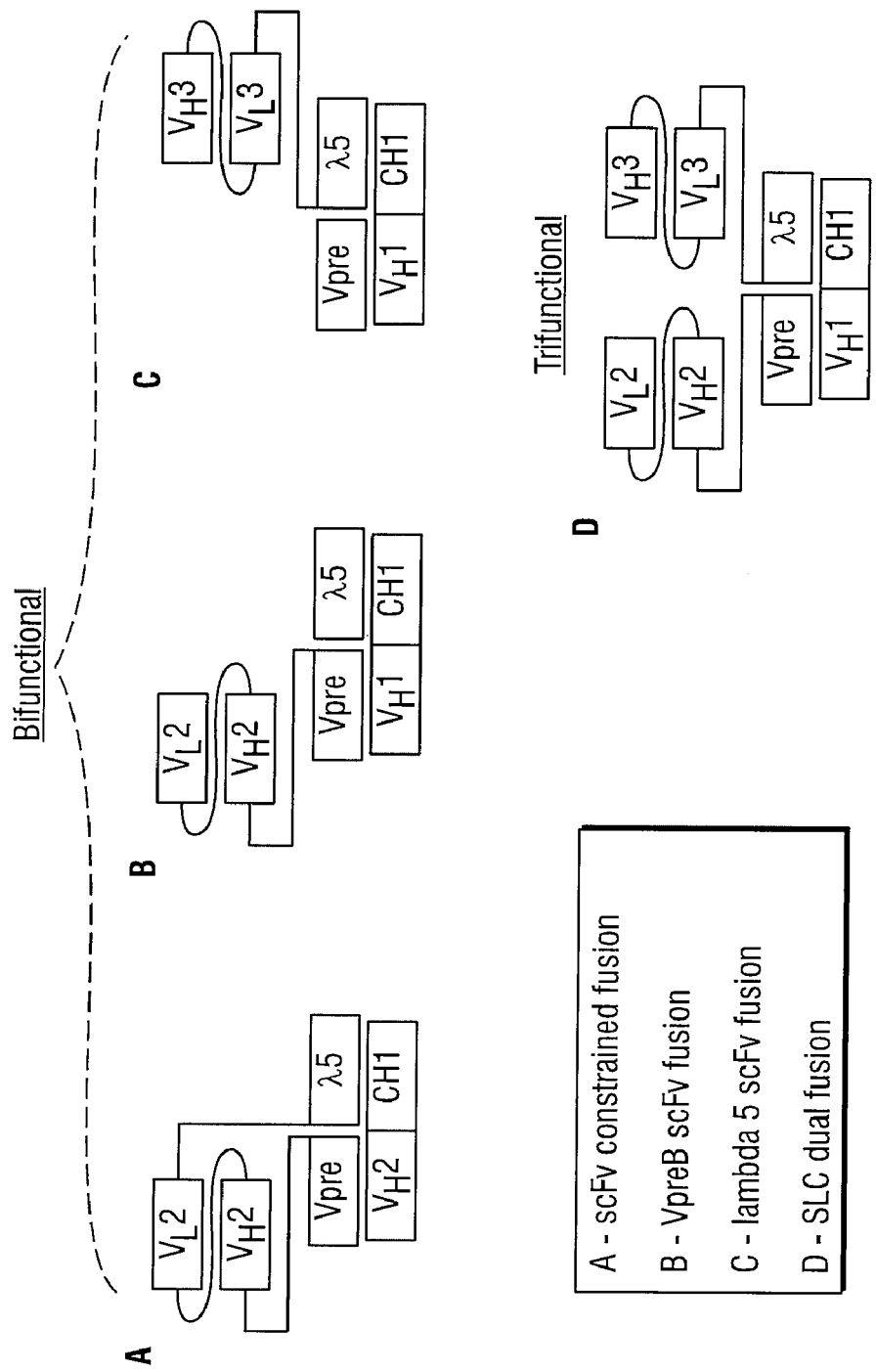
FIG. 9, structures A, B, C and D, illustrate various representative ways of adding functionality to surrogate light chain (SLC) components.

As the SLC is comprised of two independent polypeptides this creates natural opportunities to append or embed secondary functionalities. In the present Example, in the first instance an anti-VEGF scFv is inserted to create a fusion protein linking VpreB and λ5 (FIG. 9A). This resulting engineered SLC-constrained scFv is paired with the heavy chain of an anti-TNF-α antibody. The resulting construct is co-expressed with the heavy chain cloned in frame with pIII for use in phage or phagemid display. This phagemid construct is transformed into TG1 cells and a single colony is propagated in Luria Broth (LB) supplemented with 50 µg/ml Ampicillin and 2% glucose until it reached OD600 ~0.3, and infected with MK307 helper phage at 37° C. for 30 minutes without shaking. The cells are then be pelleted and then resuspended in LB containing 50 µg/ml ampicillin and 75 µg/ml kanamycin and allowed to grow overnight with vigorous aeration at 30° C. The next day the supernatant containing phagemid expressed SLC-HC fusion protein is used in Phage ELISA to determine targeted binding. Briefly the ELISA entails coating and blocking of an ELISA plate with human TNF-α or human VEGF, followed by incubation of the SLC-HC phage for 2 hours at 4° C., washing with PBS-Tween-20 (0.05%) and direct detection with anti-m13-HRP antibody.

Next a fusion of the anti-VEGF scFv to the C-terminus of VpreB is created, and the resulting tripartite protein complex construct assessed similarly to the phagemid ELISA described above.

Alternatively the an anti-ovalbumin scFv is fused to the amino terminus of λ5 and the tripartite protein complex tested for binding to both TNF-α and ovalbumin.

Finally, these two fusion constructs (VpreB-antiVEGF scFv and the λ5-anti-ovalbumin) are combined with the heavy chain of the anti-TNF-α antibody to create a trispecific molecule, which is then confirmed in phagemid ELISA as described above.

In the description scFv against disparate targets are incorporated, however one can combine functional binders to the same target to create tandem "super-binders." These tandem binders can either provide reinforced binding or even in some instances cross-linking function. Fab cross-linking will be beneficial in instances where whole antibodies provide undesirable and prolonged cross-linking. For instance, it may be undesirable for whole immunoglobulin insulin receptor antibodies that act as insulin substitutes to require 3-4 weeks for serum clearance. As insulin usually has a half-life of minutes, a Fab would be more in tune with this scale of half-life and the tandem functionality could appropriately address this application.

The above descriptions describe only antibodies as secondary functional groups, but one can also similarly incorporate relevant peptides (e.g., erythropoietin (EPO) mimetics), receptors (e.g., TNF-RI), binding proteins (e.g., IL-1ra), and any therapeutic protein, such as interferons, to the appended and constrained constructs to create molecules of similar functions.

Also one might utilize the two sites to incorporate heterodimeric proteins, such as heavy and light chains to create a secondary Fab-like molecule.

Finally, we have described only singular instances, but the incorporation of combinatorially diverse phage antibody libraries and peptide diversity libraries is also included herein, to screen with SLC candidate antibodies against their directed and desired targets.

EXAMPLE 6

Expression of Surrogate Light Chain Constructs (SURROBODY™) in Mammalian Cells

Coding sequences of the surrogate light chain components of the structures designated in FIG. 11 as "trimers" (also referred to as "SURROBODY™ variants") were cotransfected with a full-length IgG1 antibody heavy chain into CHO-K1 cells (ATCC CCL-61) to transiently produce surrogate light chain constructs for biochemical analysis. Specifically, full length human VpreB1 and λ5 were cloned into the mammalian expression vector pCI (Promega, Madison Wis.). These constructs contained their native predicted secretion signals. In the case of VpreB1 the predicted signal peptide is amino acids 1-20 of SEQ ID NO: 1, for λ5 the predicted signal sequence is amino acids 1-30 of SEQ ID NO: 5. For both of these proteins portions of their predicted nonstructural tails were deleted. For VpreB1 this included the C-terminal amino acids 122-146 of SEQ ID NO: 1 and for lambda 5 this included the N-terminal amino acids 30-86 of SEQ ID NO: 5.

The sequence of the truncated λ5 sequence in the "trimer" designated in FIG. 11 as "Lambda 5 dT" is shown as SEQ ID NO: 7. The sequence of the truncated VpreB1 sequence in the "trimer" designated in FIG. 11 as "VpreB dT" is shown as SEQ ID NO: 8.

Figure 12:
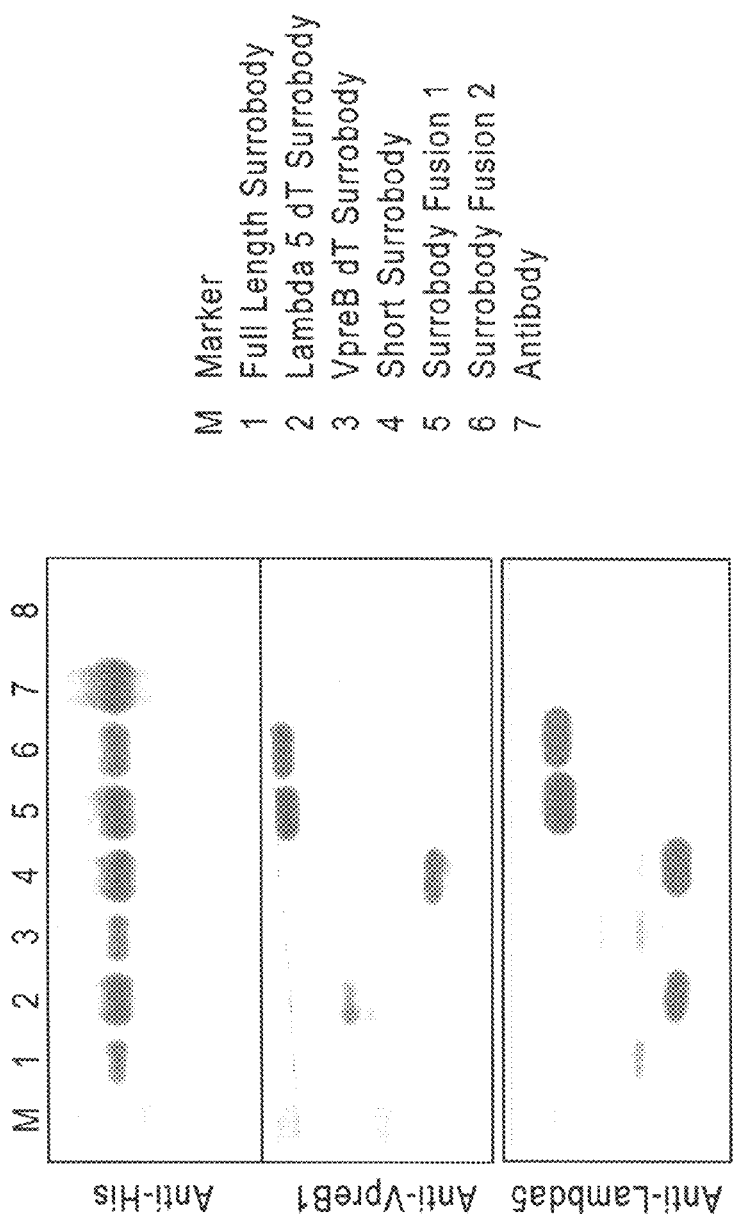
FIG. 12: Detection of surrogate light chains and conjugated heavy chains. Lane 1: Full Length; Lane 2: Lambda 5 dT; Lane 3: VpreB dt; Lane 4: Short; Lane 5: SCL fusion I; Lane 6: SLC fusion 2; Lane 7: Antibody.

Each of the four combinatorial surrogate light chain possibilities were cotransfected with a known human anti-influenza heavy chain, containing a C-terminal hexahistidine (His6) tag (SEQ ID NO: 9), and expressed according to manufacturer's suggestions (Invitrogen, Carlsbad Calif.) in low serum media. After 3 days the supernatants were collected, filtered, and purified by nickel chelate chromatography (Qiagen, Germany). The purified proteins were then examined by western blot analysis with either anti-peptide rabbit serum (VpreB and λ5) or anti-histidine antibodies (Serotec, Raleigh N.C.). Detection of proteins was visualized following anti-rabbit HRP (VpreB and λ5) or anti-mouse HRP (heavy chain) and colorimetric development with TMB substrate. (FIG. 12, lanes 1-4)

Additionally, surrogate light chain fusions (see FIG. 11) were created by engineering a chimeric protein composed of the VpreB1 gene and either the λ5 gene or the light chain constant lambda domain. Specifically a recombinantly fused protein was produced that contained amino acids 1-87 from VpreB (SEQ ID NO: 1) to λ5 protein amino acids 121-209 (SEQ ID NO: 5) (SEQ ID NO: 10). Additionally, a second fusion was made that contained amino acids 1-87 from VpreB (SEQ ID NO: 1) to the C-terminal 121 amino acid of the antibody λ light chain constant (SEQ ID NO: 11). Each surrogate light chain fusion was transiently expressed, harvested, purified, and examined by western blot analysis, essentially as described above. Notably, as both fusions contained the epitope to the anti-VpreB1 anti-peptide serum, it was used for western blot analysis. (FIG. 12, lanes 5-6)

EXAMPLE 7

Expression of Surrogate Light Chain Constructs (SURROBODY™) in *E. coli*

As recombinant proteins are often beneficially expressed in bacteria the ability of producing soluble surrogate light chain constructs in prokaryotic systems was tested. To address this, the surrogate light chain fusions designated as "dimers" in FIG. 11 were clones into *E. coli* expression/secretion systems. A plac repressible expression system was used, where the mature mammalian proteins were expressed and secreted into the periplasm by recombinant,fusion to prokaryotic leader sequences. Specifically, the surrogate light chain fusions were directed to the periplasm by fusing the coding sequence of the mature protein to the C-terminus of the m13 gIII leader coding sequence (SEQ ID NOs: 12 and 13). The heavy chain was expressed by fusing the IgG1 heavy chain variable region and heavy chain constant region domain of an anti-influenza antibody to the C-terminus of the pelB leader sequence (SEQ ID NO: 14). The plasmids expressing both proteins were transformed into HB2151 *E. coli* cells (Stratagene) and expressed overnight in LB media containing 100 mcg/ml ampicillin, and 200 micromolar IPTG at 30 degrees. The cells were harvested and periplasmic lysates were prepared, following methods known in the art. The periplasmic lysates were tested directly by western blot analysis or purified as described above (FIG. 13, panel A).

As the surrogate light chain is traditionally a component of the membrane bound preB cell receptor, it is normally found paired with an IgM class heavy chain. For our utilitarian purposes we wished to compare the ability to pair a surrogate light chain fusion with an IgM versus a IgG based constant heavy domain 1 region. To examine this we substituted a μ constant heavy domain 1 (SEQ ID NO: 15) for the gamma constant heavy domain region of the anti-influenza antibody described above. We found, from western blot analysis of the periplasmic lysates that the IgG (γ)-based constant heavy domain expressed better and purified to greater levels than a μ-based constant heavy domain based system (FIG. 13, panel B).

EXAMPLE 8

Expression of Surrogate Light Chain Constructs (SURROBODY™) m13 Phagemid

As recombinant proteins are not only usefully expressed in bacteria but also individually and in diverse library collections on the surface of bacterial virus particles we wished to produce soluble surrogate light chain constructs on the surface of m13 phagemids. To address this, surrogate light chain fusions ("dimers" in FIG. 11) were clones into *E. coli* expression/secretion systems. For all systems a pLac repressible expression system described above was used. However, in this case we appended an E-tag epitope (GAPVPYPDPLEPR) (SEQ ID NO: 16) to the surrogate light chain fusions, as well as to a light chain control protein. The sequences of the geneIII VpreB1-lambda5-E tag fusion (Fusion 1) and the geneIII VpreB1-Cl-E tag fusion (Fusion 2) are shown as SEQ ID NOs: 12 and 13, respectively. To anchor the heavy chain constructs to the m13 phagemid the heavy chain constructs were recombinantly cloned the variable heavy chains and gamma constant heavy domain 1 regions in frame with the m13 gene III product. Specifically the recombinant proteins contained an intervening, a hexahistidine peptide, the peptide epitope for the anti-c-myc antibody (GEQKLISLEEDL) (SEQ ID NO: 17), and amber stop codon. We examined the fidelity of protein expression and complex formation respectively by anti-histidine and anti-E capture ELISA.

Figure 14A:
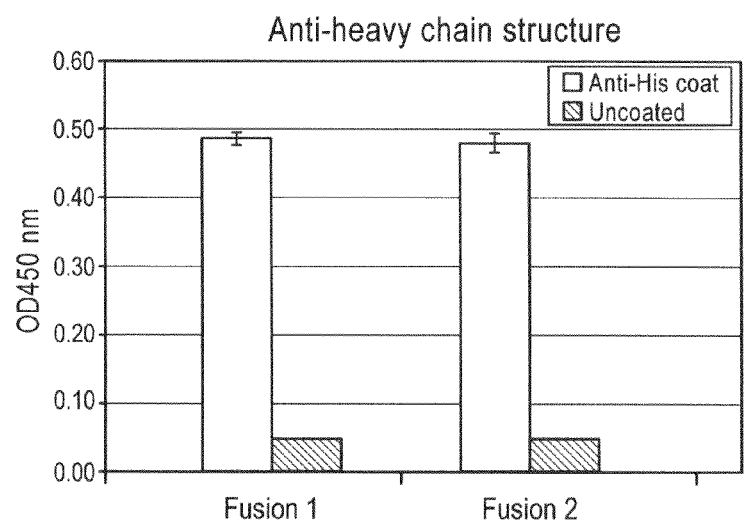
FIGS. 14A and B: Phage surrogate light chain construct capture ELISA via anti-phage detection.
Figure 14B:
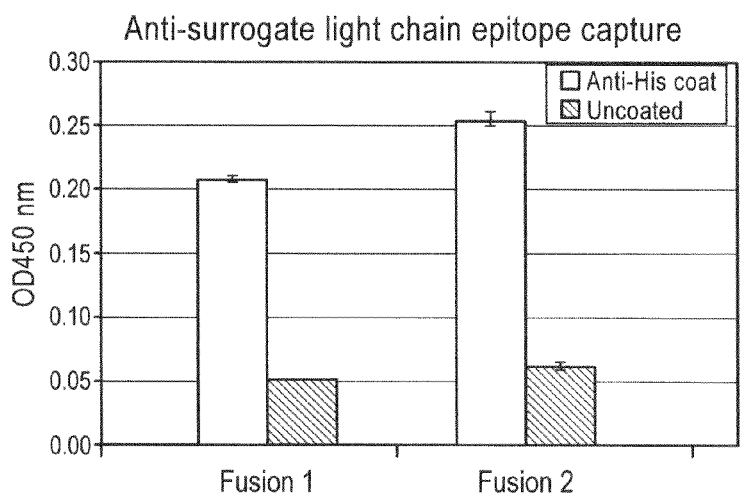

Phagemid expression of antibodies and surrobodies were accomplished by standard methods well known in the art. Essentially, TG-1 cells transformed with expression plasmids were grown to mid log (OD 600 ~0.3) in 2-YT media supplemented with 100 mcg/ml ampicillin and 2% glucose repression and then infected with m13K07 helper phage and then grown overnight in 2-YT media supplemented with 100 mcg ampicillin, 70 mcg/ml kanamycin, and 200 micromolar IPTG. Phage containing supernatants or precipitated and PBS resuspended phage were used for phage capture ELISA. The phage capture ELISA was accomplished by coating microtiter plates with either anti-histidine (Serotec) or anti-E antibodies(Abcam) and then detecting binding with anti-m13 peroxidase antibodies (Pharmacia), followed by colorimetric visualization with TMB substrate. In these instances we found specific capture of the phage by both methods, supporting high fidelity protein expression fusion to phage by the heavy chains and stable surrogate light chain association. The results are shown in FIG. 14.

EXAMPLE 9

Figure 15:
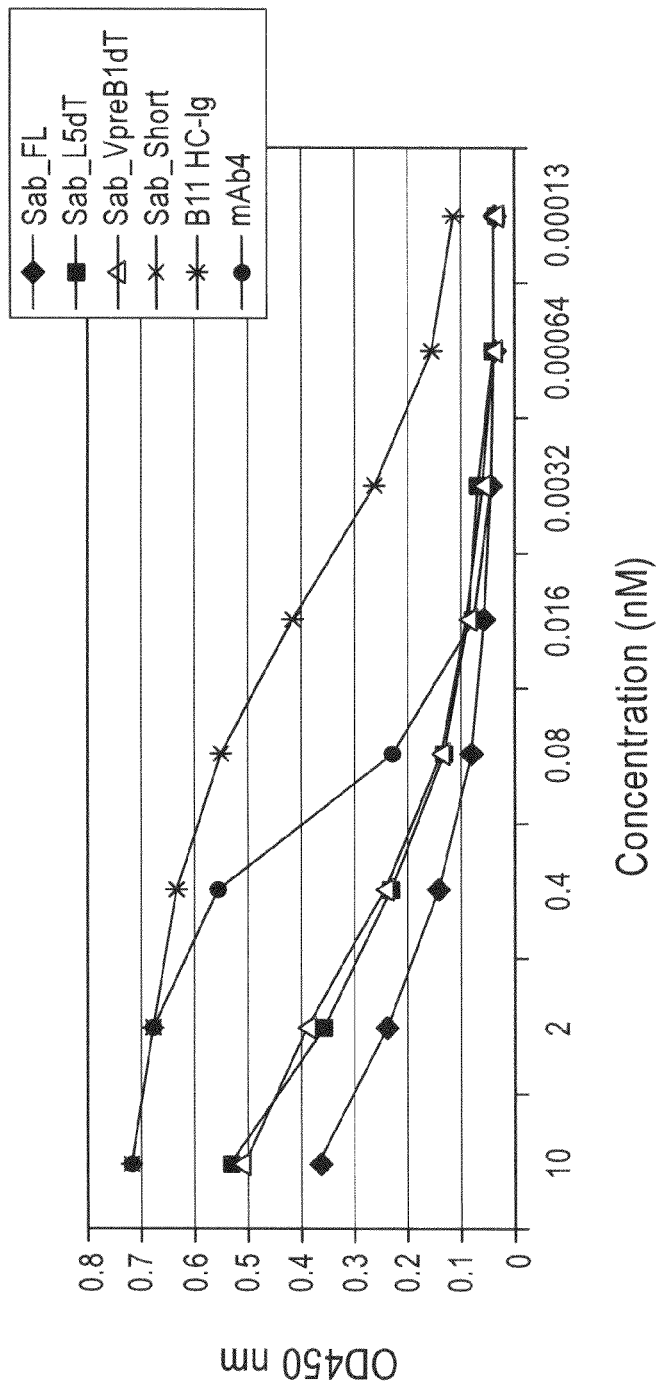
FIG. 15: Purified surrogate light chain constructs expressed in mammalian cells bind viral target.

Antigen Binding of Surrogate Light Chain Constructs Expressed in Mammalian Cells As it appeared that the surrogate light chain variants formed readily detectable complexes following nickel chelate chromatography, their ability to bind the parent antigen of cognate heavy chain partner was tested. Transient expression and purification were performed as described above. Antigen binding was tested by ELISA. Briefly, microtiter wells were coated with inactivated H5N1 Vietnam 12-3/04 virus preparations (US then incubated with quantified serially diluted purified proteins. After washing, the complexes were detected with anti-human Fc peroxidase conjugated antibodies. Finally, binding was colorimetrially visualized and quantitated with TMB substrate development (see FIG. 15).

Additionally, supernatants from transient transfections were similarly tested undiluted for antigen binding and shown in FIG. 16. After washing, the surrogate light chain complexes were detected with either anti-VpreB1 anti-peptide sera and anti-rabbit peroxidase conjugated secondary or anti-human Fc peroxidase conjugated antibodies and then colorimetrically visualized and quantitated with TMB substrate development.

EXAMPLE 10

Antigen Binding of Surrogate Light Chain Constructs Expressed in *E. coli*

Figures 17A, 17B:
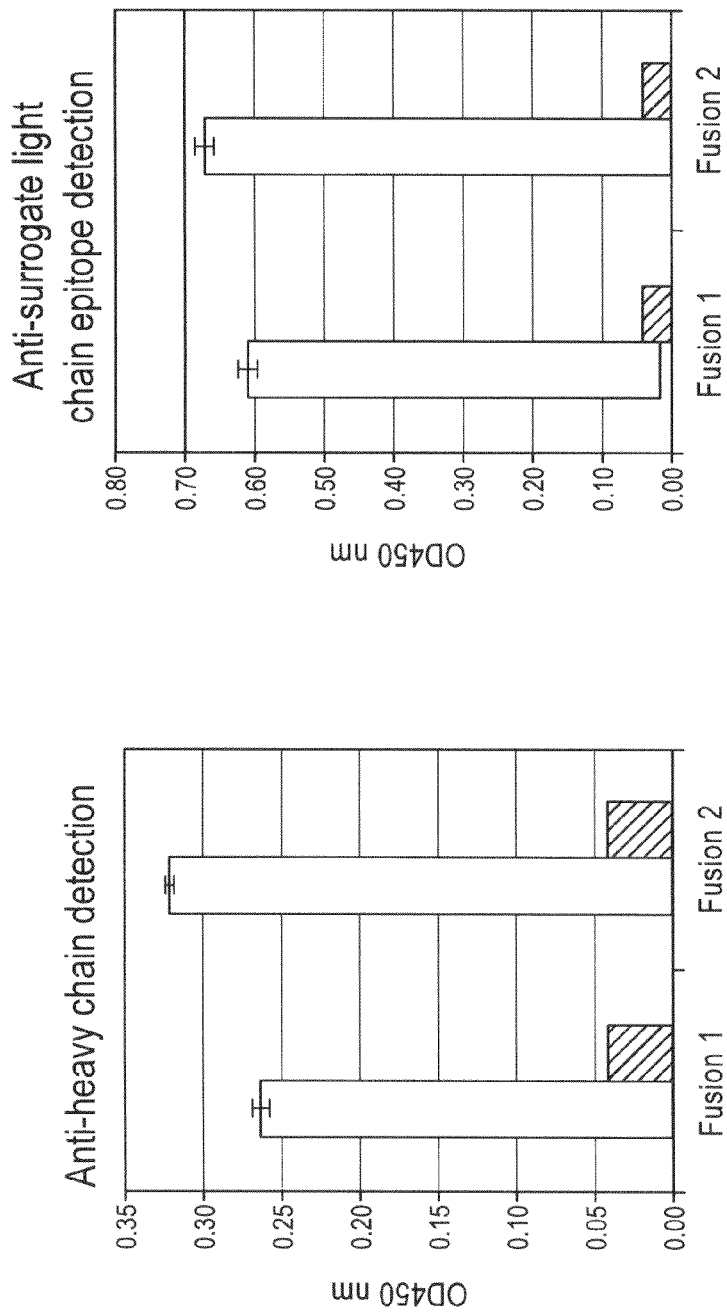
FIGS. 17A and B: Antigen binding with *E. coli* periplasmic lysates.
Figure 18:
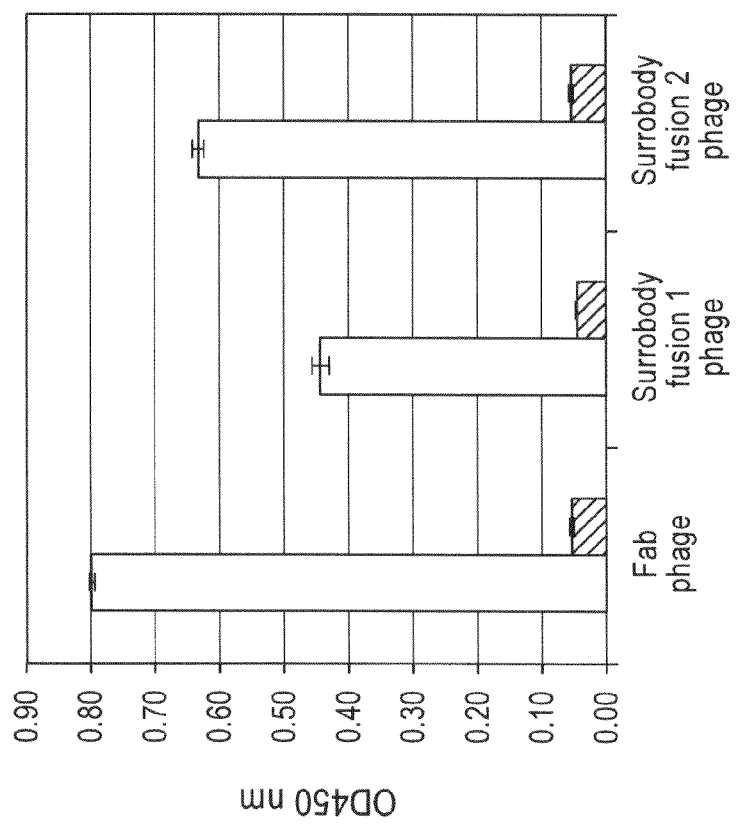
FIG. 18: Surrogate light chain fusion construct phage paired with neutralizing heavy chain readily binds H5 HA antigen.

Because the surrogate light chain fusions appeared to form stable complexes we wanted to establish whether such fusions paired with a heavy chain from and anti-influenza antibody would bind the antibody's cognate virus. To test for binding periplasmic lysates were prepared as described above. The lysates were then subjected to ELISA antigen binding, essentially as described above, except binding was detected with either a monoclonal antibody to an appended hexahistidine epitope at the C-terminus of the heavy chain or to an appended E-tag at the C-terminus of the surrogate light chain fusion via polyclonal affinity purified antibodies. Epitope detection was accomplished by either anti-mouse or anti-rabbit peroxidase conjugated antibodies. Finally, binding was colorimetrically visualized and quantitated with TMB substrate development. The results are shown in FIG. 17.

EXAMPLE 11

Antigen Binding of Phase Displayed Surrogate Light Chain Constructs

Because it was possible to make surrogate light chain variants in heterologous systems, and as phage displayed collections are desirable to future protein discovery and engineering, we wanted to determine whether the surrogate light chain variants and/or fusions were readily displayed on the surface of m13 phage as gene III-associated complexes. The variants (SEQ ID NOs: 18-22) and previously described fusions (SEQ ID NOs: 12 and 13) were coexpressed with either of two anti-influenza antibody heavy chains (SEQ ID NOs: 19 and 14) as described above and binding followed essentially the conditions also described above. Briefly, microtiter wells were coated with H5N1 Vietnam 1203/04 virus and phagemid were allowed to bind and then washed and detected directly through anti-m13 peroxidase conjugated antibodies. Binding was quantitatively determined following colorimetric substrate product formation with TMB. The results are shown in FIGS. 18 and 19.

EXAMPLE 12

Phage Surrogate Light Chain Construct Library Constructions, Selection, and Clonal ELISA An iterative approach using combinatorial antibody libraries was employed to generate and test surrogate light chain constructs that bound antigen. Briefly, combinatorial antibody libraries prepared from the bone marrow of H5N1 avian influenza survivors were created. These libraries were screened against H5N1 viral hemagglutinin protein for two rounds of selection. Next the phagemid plasmid was amplified and purified. Heavy chain variable regions isolated by restriction digest from this plasmid preparation and cloned in frame with the constant heavy domain 1 to form a recombinant fusion to the m13 gene III coat protein for phagemid display. Importantly, we used two recipient plasmids that either coexpressed a surrogate light chain fusion comprised of VpreB1 and lambda 5 (SLC fusion 1) (SEQ ID NO: 10) or VpreB1 and a constant lambda domain (SEQ ID NO: 11) from the classical lambda light chain (SLC fusion 2). The fusion 1 library produced $3.84\times10^7$ independent transformants, while the fusion 2 library produced $7.8\times10^7$ transformants. Both libraries were screened independently through two rounds and both showed significant enrichment over background (Fusion 1=5×, Fusion 2=20×) that increased in a second round of panning (Fusion 1=97×, Fusion 2=48×).

To test by ELISA for clonal antigen binding phage from both rounds and both libraries were transferred into the HB2151 *E. coli* strain to produce soluble surrobody fusion proteins. Briefly, HB2151 clones were grown and induced to produce soluble surrobodies. Specifically, colonies were cultured overnight in 2-YT media supplemented with 100 mcg/ml ampicillin and 200 micromolar IPTG overnight at 30 degrees the periplasmic lysates, as described above. The resulting periplasmic lysates were tested by ELISA, essentially as outlined above.

The number of transformants and percent positive clones for the two fusions, at rounds 1 and 2 of panning are shown in FIG. 20, and the clonal analysis data for Rounds 1 and 2 of Fusion 1 and Fusion 2 library clones are shown in FIGS. 21 and 22.

EXAMPLE 13

Surrogate Light Chain Fusions to Increase Serum Half-Life

The half-life of an antibody fragment in vivo is extended considerably when it is part of a fusion to an intact and complete heavy chain that includes all heavy chain constant domains, not just those necessary to form a stable antigen binding fragment. In the case of IgG this means the inclusion of domains CH1, CH2, and CH3. In particular it is well established that CH2 and CH3 confer the majority of this effect in vivo. In fact fusion of these CH2 and CH3 domains to heterologous proteins is typically sufficient to improve the potencies and PK/PD of these chimeric molecules compared to the parent molecules. Similarly functional fusions to the either or both VpreB and λ5 benefit by this association with the constant domains of the heavy chain.

For the treatment of type II diabetes administration of glucagon-like peptide 1 (or GLP-1) benefits individuals by inducing glucose-dependent insulin secretion in the pancreas, thereby improving glucose management in those patients. However, a long-lived GLP-1 peptide is a desirable goal. As the tails of the surrogate light chains are distinct and accessible, we could accomplish this goal by either recombinantly fusing the active GLP-1 moiety to either the C-terminus of the VpreB1 tail (SEQ ID NOs: 23 and 24) or the N-terminal tail of λ5 (SEQ ID NOs: 25 and 26). In the case of a λ5 fusion we may express this in the presence or absence of VpreB1 and even in the presence or absence of the Variable heavy domain, as depicted in FIG. 11. Fusions to VpreB1 can similarly be made in the presence or absence of λ5, and possibly with or without the CH1 domain of the heavy chain. Similarly, other beneficial growth factor, cytokine, receptor, and enzyme fusions may be created. In all of these cases binding is not requisite of the surrogate light chain, or SURROBODY™ components, but rather may be conferred either entirely or in large part by the heterologous surrogate light chain fused element.

Although in the foregoing description the invention is illustrated with reference to certain embodiments, it is not so limited. Indeed, various modifications of the invention in addition to those shown and described herein will become apparent to those skilled in the art from the foregoing description and fall within the scope of the appended claims.

EXAMPLE 14

Affinity Determination of Hemagglutinin-Binding Surrogate Light Chain Constructs To determine the affinities of fusion surrogate light chain constructs (SURROBODIES™, see, FIG. 11) we overexpressed and purified various surrobodies in *E. coli* and compared them to the parental Fabs from which the heavy chains were first identified. Affinities were determined by Bio-Layer Interferometry on a BioForte Octet essentially as follows. First, 100 μg of purified hemagglutinin protein was biotinlyated at a 20:1 molar excess using Pierce No-Weigh PEO4 biotin (cat #21329) according to manufacturer's instructions, incubated at room temperature for 1-3 hours with intermittent mixing and then incubated overnight at 4 C. The excess biotin was removed by size exclusion spin column and exchanged into PBS. Next, HA binding surrogate light chain constructs and Fabs were purified by FPLC using $Ni^{2+}$ affinity chromatography, desalted to remove excess imidazole, concentrated, and quantitated by quantitative light chain ELISAs (Bethel Labs, cat #E80-115-κ, and E80-116-λ) are performed according to the manufacturer's instructions. Finally affinities were determined by analyzing a range of sample concentrations that are typically 15 nM-500 nM in serial 2 fold dilutions. The samples were incubated with biosensors coated with HA protein for up to 15 minutes, then incubated in sample diluent for up to 1 hour. All of these steps were done with sample plate rotation at 1500 RPM. Association was measured during the Fab incubation with the HA-coated biosensors and dissociation is measured in the sample diluent incubation following binding. Affinities are shown in the following Table

| Clone | Fusion 1 VpreB1-Lambda5 | Fusion 1 VpreB1-constant lambda | Fab |
|---|---|---|---|
| F5 | 250-400 pM | 150-270 pM | 1 pM |
| B11 | 31-180 pM | Not determined | 13 pM |

All references cited throughout the specification, and the references cited therein, are hereby expressly incorporated by reference in their entirety.

The invention claimed is:

1. A polypeptide comprising amino acid residues from 1 to about 116-126 of the VpreB1 sequence of SEQ ID NO: 1, fused directly, at its C-terminus to the N-terminus of amino acid residues from about 82-93 to 209 of the λ5 sequence of SEQ ID NO: 5, conjugated to an antibody heavy chain sequence comprising a variable region to form a conjugate, wherein the conjugate specifically binds a target.

* * * * *

SEQUENCE LISTING

```
<160> NUMBER OF SEQ ID NOS: 35

<210> SEQ ID NO 1
<211> LENGTH: 145
<212> TYPE: PRT
<213> ORGANISM: Homo sapiens

<400> SEQUENCE: 1

Met Ser Trp Ala Pro Val Leu Leu Met Leu Phe Val Tyr Cys Thr Gly
  1               5                  10                  15

Cys Gly Pro Gln Pro Val Leu His Gln Pro Pro Ala Met Ser Ser Ala
             20                  25                  30

Leu Gly Thr Thr Ile Arg Leu Thr Cys Thr Leu Arg Asn Asp His Asp
         35                  40                  45

Ile Gly Val Tyr Ser Val Tyr Trp Tyr Gln Gln Arg Pro Gly His Pro
     50                  55                  60

Pro Arg Phe Leu Leu Arg Tyr Phe Ser Gln Ser Asp Lys Ser Gln Gly
 65                  70                  75                  80

Pro Gln Val Pro Pro Arg Phe Ser Gly Ser Lys Asp Val Ala Arg Asn
                 85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Glu Lys Glu Glu Arg Glu
        115                 120                 125

Arg Glu Trp Glu Glu Glu Met Glu Pro Thr Ala Ala Arg Thr Arg Val
    130                 135                 140

Pro
145

<210> SEQ ID NO 2
<211> LENGTH: 142
<212> TYPE: PRT
```

-continued

```
<213> ORGANISM: Mus sp.

<400> SEQUENCE: 2

Met Ala Trp Thr Ser Val Leu Leu Met Leu Leu Ala His Leu Thr Gly
  1               5                  10                  15

Cys Gly Pro Gln Pro Met Val His Gln Pro Pro Ser Ala Ser Ser Ser
             20                  25                  30

Leu Gly Ala Thr Ile Arg Leu Ser Cys Thr Leu Ser Asn Asp His Asn
         35                  40                  45

Ile Gly Ile Tyr Ser Ile Tyr Trp Tyr Gln Gln Arg Pro Gly His Pro
     50                  55                  60

Pro Arg Phe Leu Leu Arg Tyr Phe Ser His Ser Asp Lys His Gln Gly
 65                  70                  75                  80

Pro Asp Ile Pro Pro Arg Phe Ser Gly Ser Lys Asp Thr Ala Arg Asn
                 85                  90                  95

Leu Gly Tyr Leu Ser Ile Ser Glu Leu Gln Pro Glu Asp Glu Ala Val
            100                 105                 110

Tyr Tyr Cys Ala Val Gly Leu Arg Ser His Glu Lys Lys Arg Met Glu
        115                 120                 125

Arg Glu Trp Glu Gly Glu Lys Ser Tyr Thr Asp Leu Gly Ser
    130                 135                 140

<210> SEQ ID NO 3
<211> LENGTH: 171
<212> TYPE: PRT
<213> ORGANISM: Mus sp.

<400> SEQUENCE: 3

Met Ala Trp Thr Ser Val Leu Leu Met Leu Leu Ala His Leu Thr Gly
  1               5                  10                  15

Lys Gly Thr Leu Gly Val Gln Gly Phe Leu Ala Pro Val Ala Leu
             20                  25                  30

Leu Cys Pro Ser Asp Gly His Ala Ser Ile Phe Ser Gly Cys Gly Pro
         35                  40                  45

Gln Pro Met Val His Gln Pro Pro Ser Ala Ser Ser Ser Leu Gly Ala
     50                  55                  60

Thr Ile Arg Leu Ser Cys Thr Leu Ser Asn Asp His Asn Ile Gly Ile
 65                  70                  75                  80

Tyr Ser Ile Tyr Trp Tyr Gln Gln Arg Pro Gly His Pro Pro Arg Phe
                 85                  90                  95

Leu Leu Arg Tyr Phe Ser His Ser Asp Lys His Gln Gly Pro Asp Ile
            100                 105                 110

Pro Pro Arg Phe Ser Gly Ser Lys Asp Thr Ala Arg Asn Leu Gly Tyr
        115                 120                 125

Leu Ser Ile Ser Glu Leu Gln Pro Glu Asp Glu Ala Val Tyr Tyr Cys
    130                 135                 140

Ala Val Gly Leu Arg Ser His Glu Lys Lys Arg Met Glu Arg Glu Trp
145                 150                 155                 160

Glu Gly Glu Lys Ser Tyr Thr Asp Leu Gly Ser
                165                 170

<210> SEQ ID NO 4
<211> LENGTH: 123
<212> TYPE: PRT
<213> ORGANISM: Homo sapiens

<400> SEQUENCE: 4
```

```
Met Ala Cys Arg Cys Leu Ser Phe Leu Leu Met Gly Thr Phe Leu Ser
 1               5                  10                  15

Val Ser Gln Thr Val Leu Ala Gln Leu Asp Ala Leu Leu Val Phe Pro
                20                  25                  30

Gly Gln Val Ala Gln Leu Ser Cys Thr Leu Ser Pro Gln His Val Thr
            35                  40                  45

Ile Arg Asp Tyr Gly Val Ser Trp Tyr Gln Gln Arg Ala Gly Ser Ala
50                  55                  60

Pro Arg Tyr Leu Leu Tyr Tyr Arg Ser Glu Glu Asp His His Arg Pro
65                  70                  75                  80

Ala Asp Ile Pro Asp Arg Phe Ser Ala Ala Lys Asp Glu Ala His Asn
                85                  90                  95

Ala Cys Val Leu Thr Ile Ser Pro Val Gln Pro Glu Asp Asp Ala Asp
                100                 105                 110

Tyr Tyr Cys Ser Val Gly Tyr Gly Phe Ser Pro
            115                 120

<210> SEQ ID NO 5
<211> LENGTH: 209
<212> TYPE: PRT
<213> ORGANISM: Homo sapiens

<400> SEQUENCE: 5

Met Lys Leu Arg Val Gly Gln Thr Leu Gly Thr Ile Pro Arg Gln Cys
 1               5                  10                  15

Glu Val Leu Leu Leu Leu Leu Leu Gly Leu Val Asp Gly Val His
                20                  25                  30

His Ile Leu Ser Pro Ser Ser Ala Glu Arg Ser Arg Ala Val Gly Pro
            35                  40                  45

Gly Ala Ser Val Gly Ser Asn Arg Pro Ser Leu Trp Ala Leu Pro Gly
        50                  55                  60

Arg Leu Leu Phe Gln Ile Ile Pro Arg Gly Ala Gly Pro Arg Cys Ser
65                  70                  75                  80

Pro His Arg Leu Pro Ser Lys Pro Gln Phe Trp Tyr Val Phe Gly Gly
                85                  90                  95

Gly Thr Gln Leu Thr Ile Leu Gly Gln Pro Lys Ser Asp Pro Leu Val
                100                 105                 110

Thr Leu Phe Leu Pro Ser Leu Lys Asn Leu Gln Pro Thr Arg Pro His
            115                 120                 125

Val Val Cys Leu Val Ser Glu Phe Tyr Pro Gly Thr Leu Val Val Asp
            130                 135                 140

Trp Lys Val Asp Gly Val Pro Val Thr Gln Gly Val Glu Thr Thr Gln
145                 150                 155                 160

Pro Ser Lys Gln Thr Asn Asn Lys Tyr Met Val Ser Ser Tyr Leu Thr
                165                 170                 175

Leu Ile Ser Asp Gln Trp Met Pro His Ser Arg Tyr Ser Cys Arg Val
                180                 185                 190

Thr His Glu Gly Asn Thr Val Glu Lys Ser Val Ser Pro Ala Glu Cys
            195                 200                 205

Ser

<210> SEQ ID NO 6
<211> LENGTH: 213
<212> TYPE: PRT
<213> ORGANISM: Homo sapiens

<400> SEQUENCE: 6
```

```
Met Arg Pro Gly Thr Gly Gln Gly Gly Leu Glu Ala Pro Gly Glu Pro
 1               5                  10                  15

Gly Pro Asn Leu Arg Gln Arg Trp Pro Leu Leu Leu Gly Leu Ala
                20                  25                  30

Val Val Thr His Gly Leu Leu Arg Pro Thr Ala Ala Ser Gln Ser Arg
            35                  40                  45

Ala Leu Gly Pro Gly Ala Pro Gly Gly Ser Ser Arg Ser Ser Leu Arg
        50                  55                  60

Ser Arg Trp Gly Arg Phe Leu Leu Gln Arg Gly Ser Trp Thr Gly Pro
65                  70                  75                  80

Arg Cys Trp Pro Arg Gly Phe Gln Ser Lys His Asn Ser Val Thr His
                85                  90                  95

Val Phe Gly Ser Gly Thr Gln Leu Thr Val Leu Ser Gln Pro Lys Ala
                100                 105                 110

Thr Pro Ser Val Thr Leu Phe Pro Pro Ser Ser Glu Glu Leu Gln Ala
                115                 120                 125

Asn Lys Ala Thr Leu Val Cys Leu Met Asn Asp Phe Tyr Pro Gly Ile
            130                 135                 140

Leu Thr Val Thr Trp Lys Ala Asp Gly Thr Pro Ile Thr Gln Gly Val
145                 150                 155                 160

Glu Met Thr Thr Pro Ser Lys Gln Ser Asn Asn Lys Tyr Ala Ala Ser
                165                 170                 175

Ser Tyr Leu Ser Leu Thr Pro Glu Gln Trp Arg Ser Arg Ser Tyr
                180                 185                 190

Ser Cys Gln Val Met His Glu Gly Ser Thr Val Glu Lys Thr Val Ala
            195                 200                 205

Pro Ala Glu Cys Ser
        210

<210> SEQ ID NO 7
<211> LENGTH: 158
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 7

Met Arg Pro Gly Thr Gly Gln Gly Gly Leu Glu Ala Pro Gly Glu Pro
 1               5                  10                  15

Gly Pro Asn Leu Arg Gln Arg Trp Pro Leu Leu Leu Gly Leu Ala
                20                  25                  30

Val Val Thr His Gly Ser Val Thr His Val Phe Gly Ser Gly Thr Gln
            35                  40                  45

Leu Thr Val Leu Ser Gln Pro Lys Ala Thr Pro Ser Val Thr Leu Phe
        50                  55                  60

Pro Pro Ser Ser Glu Glu Leu Gln Ala Asn Lys Ala Thr Leu Val Cys
65                  70                  75                  80

Leu Met Asn Asp Phe Tyr Pro Gly Ile Leu Thr Val Thr Trp Lys Ala
                85                  90                  95

Asp Gly Thr Pro Ile Thr Gln Gly Val Glu Met Thr Thr Pro Ser Lys
                100                 105                 110

Gln Ser Asn Asn Lys Tyr Ala Ala Ser Ser Tyr Leu Ser Leu Thr Pro
            115                 120                 125

Glu Gln Trp Arg Ser Arg Arg Ser Tyr Ser Cys Gln Val Met His Glu
```

```
                  130                 135                 140
Gly Ser Thr Val Glu Lys Thr Val Ala Pro Ala Glu Cys Ser
145                 150                 155

<210> SEQ ID NO 8
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 8

Met Ser Trp Ala Pro Val Leu Leu Met Leu Phe Val Tyr Cys Thr Gly
  1               5                  10                  15

Cys Gly Pro Gln Pro Val Leu His Gln Pro Pro Ala Met Ser Ser Ala
                 20                  25                  30

Leu Gly Thr Thr Ile Arg Leu Thr Cys Thr Leu Arg Asn Asp His Asp
             35                  40                  45

Ile Gly Val Tyr Ser Val Tyr Trp Tyr Gln Gln Arg Pro Gly His Pro
         50                  55                  60

Pro Arg Phe Leu Leu Arg Tyr Phe Ser Gln Ser Asp Lys Ser Gln Gly
 65                  70                  75                  80

Pro Gln Val Pro Pro Arg Phe Ser Gly Ser Lys Asp Val Ala Arg Asn
                 85                  90                  95

Arg Gly Tyr Leu Ser Ile Ser Glu Leu Gln Pro Glu Asp Glu Ala Met
                100                 105                 110

Tyr Tyr Cys Ala Met Gly Ala
            115

<210> SEQ ID NO 9
<211> LENGTH: 480
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 9

Met Glu Thr Asp Thr Leu Leu Leu Trp Val Leu Leu Leu Trp Val Pro
  1               5                  10                  15

Gly Ser Thr Gly Asp Ala Gln Met Gln Leu Gln Glu Ser Gly Pro Gly
                 20                  25                  30

Leu Val Lys Pro Ser Glu Thr Leu Ser Leu Thr Cys Thr Val Ser Gly
             35                  40                  45

Tyr Ser Phe Asp Ser Gly Tyr Tyr Trp Gly Trp Leu Arg Gln Pro Pro
         50                  55                  60

Gly Lys Gly Leu Glu Trp Ile Gly Ser Ile Tyr His Ser Arg Asn Thr
 65                  70                  75                  80

Tyr Tyr Asn Pro Ser Leu Lys Ser Arg Val Thr Ile Ser Val Asp Thr
                 85                  90                  95

Ser Lys Asn Gln Phe Ser Leu Gln Leu Ser Ser Val Thr Ala Ala Asp
                100                 105                 110

Thr Ala Val Tyr Tyr Cys Ala Arg Gly Thr Trp Tyr Ser Ser Asn Leu
            115                 120                 125

Arg Tyr Trp Phe Asp Pro Trp Gly Lys Gly Thr Leu Val Arg Val Ser
        130                 135                 140
```

```
Ser Ala Ser Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
    195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
            245                 250                 255

Cys Pro Ala Pro Glu Leu Leu Gly Gly Pro Ser Val Phe Leu Phe Pro
        260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
            325                 330                 335

Leu His Gln Asp Trp Leu Asn Gly Lys Glu Tyr Lys Cys Lys Val Ser
        340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Thr Leu Pro Pro Ser Arg Glu
370                 375                 380

Glu Met Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
        420                 425                 430

Phe Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
450                 455                 460

Thr Gln Lys Ser Leu Ser Leu Ser Pro Gly His His His His His His
465                 470                 475                 480

<210> SEQ ID NO 10
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 10

Met Ser Trp Ala Pro Val Leu Leu Met Leu Phe Val Tyr Cys Thr Gly
 1               5                  10                  15

Cys Gly Pro Gln Pro Val Leu His Gln Pro Pro Ala Met Ser Ser Ala
            20                  25                  30
```

```
Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
        50                  55                  60

Pro Arg Phe Leu Leu Arg Tyr Phe Ser Gln Ser Asp Lys Ser Gln Gly
 65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Val Thr His Val Phe Gly
        115                 120                 125

Ser Gly Thr Gln Leu Thr Val Leu Ser Gln Pro Lys Ala Thr Pro Ser
    130                 135                 140

Val Thr Leu Phe Pro Pro Ser Ser Glu Glu Leu Gln Ala Asn Lys Ala
145                 150                 155                 160

Thr Leu Val Cys Leu Met Asn Asp Phe Tyr Pro Gly Ile Leu Thr Val
                165                 170                 175

Thr Trp Lys Ala Asp Gly Thr Pro Ile Thr Gln Gly Val Glu Met Thr
            180                 185                 190

Thr Pro Ser Lys Gln Ser Asn Asn Lys Tyr Ala Ala Ser Ser Tyr Leu
        195                 200                 205

Ser Leu Thr Pro Glu Gln Trp Arg Ser Arg Arg Ser Tyr Ser Cys Gln
    210                 215                 220

Val Met His Glu Gly Ser Thr Val Glu Lys Thr Val Ala Pro Ala Glu
225                 230                 235                 240

Cys Ser

<210> SEQ ID NO 11
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"
<220> FEATURE:
<221> NAME/KEY: MOD_RES
<222> LOCATION: (153)..(153)
<223> OTHER INFORMATION: Any amino acid

<400> SEQUENCE: 11

Met Ser Trp Ala Pro Val Leu Leu Met Leu Phe Val Tyr Cys Thr Gly
 1               5                  10                  15

Cys Gly Pro Gln Pro Val Leu His Gln Pro Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala Arg Ser Ser Val Thr His Val Phe Gly
```

```
            115                 120                 125
Ser Gly Thr Gln Leu Thr Val Leu Gly Gln Pro Lys Ala Ala Pro Ser
        130                 135                 140

Val Thr Leu Phe Pro Pro Ser Ser Xaa Glu Leu Gln Ala Asn Lys Ala
145                 150                 155                 160

Thr Leu Val Cys Leu Ile Ser Asp Phe Tyr Pro Gly Ala Val Thr Val
                165                 170                 175

Ala Trp Lys Ala Asp Ser Ser Pro Val Lys Ala Gly Val Glu Thr Thr
                180                 185                 190

Thr Pro Ser Lys Gln Ser Asn Asn Lys Tyr Ala Ala Ser Ser Tyr Leu
            195                 200                 205

Ser Leu Thr Pro Glu Gln Trp Lys Ser His Arg Ser Tyr Ser Cys Gln
        210                 215                 220

Val Thr His Glu Gly Ser Thr Val Glu Lys Thr Val Ala Pro Ala Glu
225                 230                 235                 240

Cys Ser

<210> SEQ ID NO 12
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 12

Val Lys Lys Leu Leu Leu Phe Ala Ile Pro Leu Val Val Pro Phe Tyr
1               5                   10                  15

Ser His Ser Ala Gln Pro Val Leu His Gln Pro Pro Ala Met Ser Ser
            20                  25                  30

Ala Leu Gly Thr Thr Ile Arg Leu Thr Cys Thr Leu Arg Asn Asp His
        35                  40                  45

Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
            100                 105                 110

Met Tyr Tyr Cys Ala Met Gly Ala Arg Ser Ser Val Thr His Val Phe
        115                 120                 125

Gly Ser Gly Thr Gln Leu Thr Val Leu Ser Gln Pro Lys Ala Thr Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175

Val Thr Trp Lys Ala Asp Gly Thr Pro Ile Thr Gln Gly Val Glu Met
                180                 185                 190

Thr Thr Pro Ser Lys Gln Ser Asn Asn Lys Tyr Ala Ala Ser Ser Tyr
            195                 200                 205

Leu Ser Leu Thr Pro Glu Gln Trp Arg Ser Arg Ser Tyr Ser Cys
        210                 215                 220

Gln Val Met His Glu Gly Ser Thr Val Glu Lys Thr Val Ala Pro Ala
```

```
                225                 230                 235                 240
Glu Cys Ser Gly Ala Pro Val Pro Tyr Pro Asp Pro Leu Glu Pro Arg
                245                 250                 255
```

<210> SEQ ID NO 13
<211> LENGTH: 256
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 13

```
Val Lys Lys Leu Leu Phe Ala Ile Pro Leu Val Val Pro Phe Tyr
 1               5                  10                  15

Ser His Ser Ala Gln Pro Val Leu His Gln Pro Ala Met Ser Ser
                20                  25                  30

Ala Leu Gly Thr Thr Ile Arg Leu Thr Cys Thr Leu Arg Asn Asp His
                35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
 65                 70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
                100                 105                 110

Met Tyr Tyr Cys Ala Met Gly Ala Arg Ser Ser Val Thr His Val Phe
            115                 120                 125

Gly Ser Gly Thr Gln Leu Thr Val Leu Arg Gln Pro Lys Ala Ala Pro
130                 135                 140

Ser Val Thr Leu Phe Pro Pro Ser Ser Glu Glu Leu Gln Ala Asn Lys
145                 150                 155                 160

Ala Thr Leu Val Cys Leu Ile Ser Asp Phe Tyr Pro Gly Ala Val Thr
                165                 170                 175

Val Ala Trp Lys Ala Asp Gly Ser Pro Val Lys Ala Gly Val Glu Thr
                180                 185                 190

Thr Thr Pro Ser Lys Gln Ser Asn Asn Lys Tyr Ala Ala Ser Ser Tyr
            195                 200                 205

Leu Ser Leu Thr Pro Glu Gln Trp Lys Ser His Lys Ser Tyr Ser Cys
210                 215                 220

Gln Val Thr His Glu Gly Ser Thr Val Glu Lys Thr Val Ala Pro Thr
225                 230                 235                 240

Glu Cys Ser Gly Ala Pro Val Pro Tyr Pro Asp Pro Leu Glu Pro Arg
                245                 250                 255
```

<210> SEQ ID NO 14
<211> LENGTH: 269
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 14

```
Met Lys Tyr Leu Leu Pro Thr Ala Ala Ala Gly Leu Leu Leu Leu Ala
 1               5                  10                  15
```

```
Ala Gln Pro Ala Met Ala Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Phe Pro Phe Ser Ser Tyr Val Met Ile Trp Val Arg Gln Val Pro Gly
    50                  55                  60

Lys Gly Leu Glu Trp Val Ser Ala Ile Gly Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Asp Asp
            100                 105                 110

Thr Ala Val Tyr Tyr Cys Val Leu Ser Pro Lys Ser Tyr Tyr Asp Asn
        115                 120                 125

Ser Gly Ile Tyr Phe Asp Phe Trp Gly Lys Gly Thr Leu Val Arg Val
    130                 135                 140

Ser Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Ser Leu Gly Thr
    210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Ala Ala Ala His His His His
                245                 250                 255

His His Gly Glu Gln Lys Leu Ile Ser Glu Glu Asp Leu
            260                 265

<210> SEQ ID NO 15
<211> LENGTH: 271
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 15

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Glu Ser Gly Gly Gly
            20                  25                  30

Leu Val Gln Pro Gly Gly Ser Leu Arg Leu Ser Cys Ala Ala Ser Gly
        35                  40                  45

Phe Pro Phe Ser Ser Tyr Val Met Ile Trp Val Arg Gln Val Pro Gly
    50                  55                  60

Lys Gly Leu Glu Trp Val Ser Ala Ile Gly Gly Ser Gly Gly Ser Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Asp Asp
            100                 105                 110
```

```
Thr Ala Val Tyr Tyr Cys Val Leu Ser Pro Lys Ser Tyr Tyr Asp Asn
            115                 120                 125

Ser Gly Ile Tyr Phe Asp Phe Trp Gly Lys Gly Thr Leu Val Arg Val
        130                 135                 140

Ser Ser Gly Ser Ala Ser Ala Pro Thr Leu Phe Pro Leu Val Ser Cys
145                 150                 155                 160

Glu Asn Ser Pro Ser Asp Thr Ser Ser Val Ala Val Gly Cys Leu Ala
                165                 170                 175

Gln Asp Phe Leu Pro Asp Ser Ile Thr Phe Ser Trp Lys Tyr Lys Asn
            180                 185                 190

Asn Ser Asp Ile Ser Ser Thr Arg Gly Phe Pro Ser Val Leu Arg Gly
        195                 200                 205

Gly Lys Tyr Ala Ala Thr Ser Gln Val Leu Leu Pro Ser Lys Asp Val
    210                 215                 220

Met Gln Gly Thr Asp Glu His Val Val Cys Lys Val Gln His Pro Asn
225                 230                 235                 240

Gly Asn Lys Glu Lys Asn Val Pro Leu Pro Val Ala Ala Ala His His
                245                 250                 255

His His His His Gly Glu Gln Lys Leu Ile Ser Glu Glu Asp Leu
            260                 265                 270

<210> SEQ ID NO 16
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Gly Ala Pro Val Pro Tyr Pro Asp Pro Leu Glu Pro Arg
1               5                   10

<210> SEQ ID NO 17
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Gly Glu Gln Lys Leu Ile Ser Leu Glu Glu Asp Leu
1               5                   10

<210> SEQ ID NO 18
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 18

Val Lys Lys Leu Leu Leu Phe Ala Ile Pro Leu Val Val Pro Phe Tyr
1               5                   10                  15

Ser His Ser Ala Gln Pro Val Leu His Gln Pro Pro Ala Met Ser Ser
            20                  25                  30

Ala Leu Gly Thr Thr Ile Arg Leu Thr Cys Thr Leu Arg Asn Asp His
```

```
Asp Ile Gly Val Tyr Ser Val Tyr Trp Tyr Gln Gln Arg Pro Gly His
            50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
                100                 105                 110

Met Tyr Tyr Cys Ala Met Gly Ala Arg Ser Ser Glu Lys Glu Glu Arg
            115                 120                 125

Glu Arg Glu Trp Glu Glu Met Glu Pro Thr Ala Ala Arg Thr Arg
130                 135                 140

Val Pro Gly Ala Pro Val Pro Tyr Pro Asp Pro Leu Glu Pro Arg
145                 150                 155
```

<210> SEQ ID NO 19
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence: Synthetic construct"

<400> SEQUENCE: 19

```
Val Lys Lys Leu Leu Leu Phe Ala Ile Pro Leu Val Val Pro Phe Tyr
 1               5                  10                  15

Ser His Ser Ala Gln Pro Val Leu His Gln Pro Pro Ala Met Ser Ser
                20                  25                  30

Ala Leu Gly Thr Thr Ile Arg Leu Thr Cys Thr Leu Arg Asn Asp His
            35                  40                  45

Asp Ile Gly Val Tyr Ser Val Tyr Trp Tyr Gln Gln Arg Pro Gly His
        50                  55                  60

Pro Pro Arg Phe Leu Leu Arg Tyr Phe Ser Gln Ser Asp Lys Ser Gln
 65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
                100                 105                 110

Met Tyr Tyr Cys Ala Met Gly Ala
            115                 120
```

<210> SEQ ID NO 20
<211> LENGTH: 133
<212> TYPE: PRT
<213> ORGANISM: Artificial Sequence
<220> FEATURE:
<221> NAME/KEY: source
<223> OTHER INFORMATION: /note="Description of Artificial Sequence: Synthetic construct"

<400> SEQUENCE: 20

```
Val Lys Lys Leu Leu Leu Phe Ala Ile Pro Leu Val Val Pro Phe Tyr
 1               5                  10                  15

Ser His Ser Ala Gln Pro Val Leu His Gln Pro Pro Ala Met Ser Ser
                20                  25                  30

Ala Leu Gly Thr Thr Ile Arg Leu Thr Cys Thr Leu Arg Asn Asp His
            35                  40                  45
```

```
Asp Ile Gly Val Tyr Ser Val Tyr Trp Tyr Gln Gln Arg Pro Gly His
    50                  55                  60

Pro Pro Arg Phe Leu Leu Arg Tyr Phe Ser Gln Ser Asp Lys Ser Gln
65                  70                  75                  80

Gly Pro Gln Val Pro Pro Arg Phe Ser Gly Ser Lys Asp Val Ala Arg
                85                  90                  95

Asn Arg Gly Tyr Leu Ser Ile Ser Glu Leu Gln Pro Glu Asp Glu Ala
                100                 105                 110

Met Tyr Tyr Cys Ala Met Gly Ala Gly Ala Pro Val Pro Tyr Pro Asp
                115                 120                 125

Pro Leu Glu Pro Arg
            130
```

```
<210> SEQ ID NO 21
<211> LENGTH: 198
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 21
```

```
Met Lys Lys Thr Ala Ile Ala Ile Ala Val Ala Leu Ala Gly Phe Ala
1               5                   10                  15

Thr Val Ala Gln Ala Ala Leu Leu Arg Pro Thr Ala Ala Ser Gln Ser
                20                  25                  30

Arg Ala Leu Gly Pro Gly Ala Pro Gly Gly Ser Ser Arg Ser Ser Leu
            35                  40                  45

Arg Ser Arg Trp Gly Arg Phe Leu Leu Gln Arg Gly Ser Trp Thr Gly
50                  55                  60

Pro Arg Cys Trp Pro Arg Gly Phe Gln Ser Lys His Asn Ser Val Thr
65                  70                  75                  80

His Val Phe Gly Ser Gly Thr Gln Leu Thr Val Leu Ser Gln Pro Lys
                85                  90                  95

Ala Thr Pro Ser Val Thr Leu Phe Pro Pro Ser Ser Glu Glu Leu Gln
                100                 105                 110

Ala Asn Lys Ala Thr Leu Val Cys Leu Met Asn Asp Phe Tyr Pro Gly
                115                 120                 125

Ile Leu Thr Val Thr Trp Lys Ala Asp Gly Thr Pro Ile Thr Gln Gly
                130                 135                 140

Val Glu Met Thr Thr Pro Ser Lys Gln Ser Asn Asn Lys Tyr Ala Ala
145                 150                 155                 160

Ser Ser Tyr Leu Ser Leu Thr Pro Glu Gln Trp Arg Ser Arg Arg Ser
                165                 170                 175

Tyr Ser Cys Gln Val Met His Glu Gly Ser Thr Val Glu Lys Thr Val
                180                 185                 190

Ala Pro Ala Glu Cys Ser
            195
```

```
<210> SEQ ID NO 22
<211> LENGTH: 143
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 22
```

```
Met Lys Lys Thr Ala Ile Ala Ile Ala Val Ala Leu Ala Gly Phe Ala
1               5                   10                  15

Thr Val Ala Gln Ala Ala Ser Val Thr His Val Phe Gly Ser Gly Thr
                20                  25                  30

Gln Leu Thr Val Leu Ser Gln Pro Lys Ala Thr Pro Ser Val Thr Leu
            35                  40                  45

Phe Pro Pro Ser Ser Glu Glu Leu Gln Ala Asn Lys Ala Thr Leu Val
    50                  55                  60

Cys Leu Met Asn Asp Phe Tyr Pro Gly Ile Leu Thr Val Thr Trp Lys
65                  70                  75                  80

Ala Asp Gly Thr Pro Ile Thr Gln Gly Val Glu Met Thr Thr Pro Ser
                85                  90                  95

Lys Gln Ser Asn Asn Lys Tyr Ala Ala Ser Ser Tyr Leu Ser Leu Thr
                100                 105                 110

Pro Glu Gln Trp Arg Ser Arg Arg Ser Tyr Ser Cys Gln Val Met His
            115                 120                 125

Glu Gly Ser Thr Val Glu Lys Thr Val Ala Pro Ala Glu Cys Ser
            130                 135                 140

<210> SEQ ID NO 23
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 23

Met Ser Trp Ala Pro Val Leu Leu Met Leu Phe Val Tyr Cys Thr Gly
1               5                   10                  15

Cys Gly Pro Gln Pro Val Leu His Gln Pro Pro Ala Met Ser Ser Ala
                20                  25                  30

Leu Gly Thr Thr Ile Arg Leu Thr Cys Thr Leu Arg Asn Asp His Asp
            35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
                100                 105                 110

Tyr Tyr Cys Ala Met Gly Ala Arg Ser Ser Glu Lys Glu Glu Arg Glu
            115                 120                 125

Arg Glu Trp Glu Glu Glu Met Glu Pro Thr Ala Arg Thr Arg Val
            130                 135                 140

Pro His Ala Glu Gly Thr Phe Thr Ser Asp Val Ser Ser Tyr Leu Glu
145                 150                 155                 160

Gly Gln Ala Ala Lys Glu Phe Ile Ala Trp Leu Val Lys Gly Arg
                165                 170                 175

<210> SEQ ID NO 24
<211> LENGTH: 149
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic construct"

<400> SEQUENCE: 24

```
Met Ser Trp Ala Pro Val Leu Leu Met Leu Phe Val Tyr Cys Thr Gly
1               5                   10                  15

Cys Gly Pro Gln Pro Val Leu His Gln Pro Ala Met Ser Ser Ala
            20                  25                  30

Leu Gly Thr Thr Ile Arg Leu Thr Cys Thr Leu Arg Asn Asp His Asp
        35                  40                  45

Ile Gly Val Tyr Ser Val Tyr Trp Tyr Gln Gln Arg Pro Gly His Pro
    50                  55                  60

Pro Arg Phe Leu Leu Arg Tyr Phe Ser Gln Ser Asp Lys Ser Gln Gly
65                  70                  75                  80

Pro Gln Val Pro Pro Arg Phe Ser Gly Ser Lys Asp Val Ala Arg Asn
                85                  90                  95

Arg Gly Tyr Leu Ser Ile Ser Glu Leu Gln Pro Glu Asp Glu Ala Met
            100                 105                 110

Tyr Tyr Cys Ala Met Gly Ala His Ala Glu Gly Thr Phe Thr Ser Asp
        115                 120                 125

Val Ser Ser Tyr Leu Glu Gly Gln Ala Ala Lys Glu Phe Ile Ala Trp
    130                 135                 140

Leu Val Lys Gly Arg
145
```

<210> SEQ ID NO 25
<211> LENGTH: 243
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 25

```
Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu His Ala Glu
            20                  25                  30

Gly Thr Phe Thr Ser Asp Val Ser Ser Tyr Leu Glu Gly Gln Ala Ala
        35                  40                  45

Lys Glu Phe Ile Ala Trp Leu Val Lys Gly Arg Gly Leu Ala Val Val
    50                  55                  60

Thr His Gly Leu Leu Arg Pro Thr Ala Ala Ser Gln Ser Arg Ala Leu
65                  70                  75                  80

Gly Pro Gly Ala Pro Gly Ser Ser Arg Ser Ser Leu Arg Ser Arg
                85                  90                  95

Trp Gly Arg Phe Leu Leu Gln Arg Gly Ser Trp Thr Pro Arg Cys
            100                 105                 110

Trp Pro Arg Gly Phe Gln Ser Lys His Asn Ser Val Thr His Val Phe
        115                 120                 125

Gly Ser Gly Thr Gln Leu Thr Val Leu Ser Gln Pro Lys Ala Thr Pro
    130                 135                 140

Ser Val Thr Leu Phe Pro Pro Ser Ser Glu Glu Leu Gln Ala Asn Lys
145                 150                 155                 160

Ala Thr Leu Val Cys Leu Met Asn Asp Phe Tyr Pro Gly Ile Leu Thr
                165                 170                 175
```

```
Val Thr Trp Lys Ala Asp Gly Thr Pro Ile Thr Gln Gly Val Glu Met
            180                 185                 190

Thr Thr Pro Ser Lys Gln Ser Asn Asn Lys Tyr Ala Ala Ser Ser Tyr
        195                 200                 205

Leu Ser Leu Thr Pro Glu Gln Trp Arg Ser Arg Ser Tyr Ser Cys
210                 215                 220

Gln Val Met His Glu Gly Ser Thr Val Glu Lys Thr Val Ala Pro Ala
225             230                 235                 240

Glu Cys Ser

<210> SEQ ID NO 26
<211> LENGTH: 188
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic construct"

<400> SEQUENCE: 26

Met Arg Pro Gly Thr Gly Gln Gly Gly Leu Glu Ala Pro Gly Glu Pro
1               5                   10                  15

Gly Pro Asn Leu Arg Gln Arg Trp Pro Leu Leu Leu Gly His Ala
            20                  25                  30

Glu Gly Thr Phe Thr Ser Asp Val Ser Ser Tyr Leu Glu Gly Gln Ala
            35                  40                  45

Ala Lys Glu Phe Ile Ala Trp Leu Val Lys Gly Arg Leu Ala Val Val
        50                  55                  60

Thr His Gly Ser Val Thr His Val Phe Gly Ser Gly Thr Gln Leu Thr
65              70                  75                  80

Val Leu Ser Gln Pro Lys Ala Thr Pro Ser Val Thr Leu Phe Pro Pro
                85                  90                  95

Ser Ser Glu Glu Leu Gln Ala Asn Lys Ala Thr Leu Val Cys Leu Met
                100                 105                 110

Asn Asp Phe Tyr Pro Gly Ile Leu Thr Val Thr Trp Lys Ala Asp Gly
            115                 120                 125

Thr Pro Ile Thr Gln Gly Val Glu Met Thr Thr Pro Ser Lys Gln Ser
        130                 135                 140

Asn Asn Lys Tyr Ala Ala Ser Ser Tyr Leu Ser Leu Thr Pro Glu Gln
145                 150                 155                 160

Trp Arg Ser Arg Ser Tyr Ser Cys Gln Val Met His Glu Gly Ser
                165                 170                 175

Thr Val Glu Lys Thr Val Ala Pro Ala Glu Cys Ser
            180                 185

<210> SEQ ID NO 27
<211> LENGTH: 105
<212> TYPE: PRT
<213> ORGANISM: Homo sapiens

<400> SEQUENCE: 27

Gly Ser Gln Ser Val Leu Thr Gln Pro Pro Ser Val Ser Ala Ala Pro
1               5                   10                  15

Gly Gln Lys Val Thr Ile Ser Cys Ser Gly Ser Ser Ser Asn Ile Gly
            20                  25                  30

Asn Asn Tyr Val Ser Trp Tyr Gln Gln Leu Pro Gly Thr Ala Pro Lys
            35                  40                  45

Leu Leu Ile Tyr Asp Asn Asn Lys Arg Pro Ser Gly Ile Pro Asp Arg
```

```
            50                  55                  60
Phe Ser Gly Ser Lys Ser Gly Thr Ser Ala Thr Leu Gly Ile Thr Gly
 65                  70                  75                  80

Leu Gln Thr Gly Asp Glu Ala Asp Tyr Tyr Cys Gly Thr Trp Asp Ser
                 85                  90                  95

Ser Leu Ser Ala Val Val Phe Gly Gly
            100                 105

<210> SEQ ID NO 28
<211> LENGTH: 114
<212> TYPE: PRT
<213> ORGANISM: Homo sapiens

<400> SEQUENCE: 28

Gly Gly Thr Lys Leu Thr Val Leu Arg Gln Pro Lys Ala Ala Pro Ser
 1               5                  10                  15

Val Thr Leu Phe Pro Pro Ser Ser Glu Glu Leu Gln Ala Asn Lys Ala
                 20                  25                  30

Thr Leu Val Cys Leu Ile Ser Asp Phe Tyr Pro Gly Ala Val Thr Val
             35                  40                  45

Ala Trp Lys Ala Asp Gly Ser Pro Val Lys Ala Gly Val Glu Thr Thr
 50                  55                  60

Thr Pro Ser Lys Gln Ser Asn Asn Lys Tyr Ala Ala Ser Ser Tyr Leu
 65                  70                  75                  80

Ser Leu Thr Pro Glu Gln Trp Lys Ser His Lys Ser Tyr Ser Cys Gln
                 85                  90                  95

Val Thr His Glu Gly Ser Thr Val Glu Lys Thr Val Ala Pro Thr Glu
            100                 105                 110

Cys Ser

<210> SEQ ID NO 29
<211> LENGTH: 105
<212> TYPE: PRT
<213> ORGANISM: Homo sapiens

<400> SEQUENCE: 29

Gln Pro Val Leu Thr Gln Pro Ser Ser His Ser Ala Ser Ser Gly Ala
 1               5                  10                  15

Ser Val Arg Leu Thr Cys Met Leu Ser Ser Gly Phe Ser Val Gly Asp
                 20                  25                  30

Phe Trp Ile Arg Trp Tyr Gln Gln Lys Pro Gly Asn Pro Pro Arg Tyr
             35                  40                  45

Leu Leu Tyr Tyr His Ser Asp Ser Asn Lys Gly Gln Gly Ser Gly Val
 50                  55                  60

Pro Ser Arg Phe Ser Gly Ser Asn Asp Ala Ser Ala Asn Ala Gly Ile
 65                  70                  75                  80

Leu Arg Ile Ser Gly Leu Gln Pro Glu Asp Glu Ala Asp Tyr Tyr Cys
                 85                  90                  95

Gly Thr Trp His Ser Asn Ser Lys Thr
            100                 105

<210> SEQ ID NO 30
<211> LENGTH: 104
<212> TYPE: PRT
<213> ORGANISM: Homo sapiens

<400> SEQUENCE: 30

Gln Ala Val Leu Thr Gln Pro Ala Ser Leu Ser Ala Ser Pro Gly Ala
```

```
                1               5                  10                 15
    Ser Ala Ser Leu Thr Cys Thr Leu Arg Ser Gly Ile Asn Val Gly Thr
                    20                     25                 30

Tyr Arg Ile Tyr Trp Tyr Gln Gln Lys Pro Gly Ser Pro Pro Gln Tyr
                    35                     40                 45

Leu Leu Arg Tyr Lys Ser Asp Ser Asp Lys Gln Gln Gly Ser Gly Val
                    50                     55                 60

Pro Ser Arg Phe Ser Gly Ser Lys Asp Ala Ser Ala Asn Ala Gly Ile
     65                     70                     75                 80

Leu Leu Ile Ser Gly Leu Gln Ser Glu Asp Glu Ala Asp Tyr Tyr Cys
                    85                     90                 95

Met Ile Trp His Ser Ser Ala Ser
                    100

<210> SEQ ID NO 31
<211> LENGTH: 104
<212> TYPE: PRT
<213> ORGANISM: Homo sapiens

<400> SEQUENCE: 31

Gln Pro Val Leu Thr Gln Pro Ser Ser Ala Ser Pro Gly Glu
      1               5                  10                 15

Ser Ala Arg Leu Thr Cys Thr Leu Pro Ser Asp Ile Asn Val Gly Ser
                    20                     25                 30

Tyr Asn Ile Tyr Trp Tyr Gln Gln Lys Pro Gly Ser Pro Pro Arg Tyr
                    35                     40                 45

Leu Leu Tyr Tyr Tyr Ser Asp Ser Asp Lys Gly Gln Gly Ser Gly Val
                    50                     55                 60

Pro Ser Arg Phe Ser Gly Ser Lys Asp Ala Ser Ala Asn Thr Gly Ile
     65                     70                     75                 80

Leu Leu Ile Ser Gly Leu Gln Ser Glu Asp Glu Ala Asp Tyr Tyr Cys
                    85                     90                 95

Met Ile Trp Pro Ser Asn Ala Ser
                    100

<210> SEQ ID NO 32
<211> LENGTH: 113
<212> TYPE: PRT
<213> ORGANISM: Homo sapiens

<400> SEQUENCE: 32

Gly Thr Lys Leu Thr Val Leu Arg Gln Pro Lys Ala Ala Pro Ser Val
      1               5                  10                 15

Thr Leu Phe Pro Pro Ser Ser Glu Glu Leu Gln Ala Asn Lys Ala Thr
                    20                     25                 30

Leu Val Cys Leu Ile Ser Asp Phe Tyr Pro Gly Ala Val Thr Val Ala
                    35                     40                 45

Trp Lys Ala Asp Gly Ser Pro Val Lys Ala Gly Val Glu Thr Thr Thr
                    50                     55                 60

Pro Ser Lys Gln Ser Asn Asn Lys Tyr Ala Ala Ser Ser Tyr Leu Ser
     65                     70                     75                 80

Leu Thr Pro Glu Gln Trp Lys Ser His Lys Ser Tyr Ser Cys Gln Val
                    85                     90                 95

Thr His Glu Gly Ser Thr Val Glu Lys Thr Val Ala Pro Thr Glu Cys
                    100                    105                110

Ser
```

```
<210> SEQ ID NO 33
<211> LENGTH: 107
<212> TYPE: PRT
<213> ORGANISM: Homo sapiens

<400> SEQUENCE: 33

Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
 65                 70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 34
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 34

His His His His His His
 1               5

<210> SEQ ID NO 35
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Gly Gly Gly Gly Ser Gly Gly Gly Gly Ser Gly Gly Gly Gly Ser
 1               5                  10                  15
```